United States Patent
Pushpala et al.

(10) Patent No.: US 11,197,985 B2
(45) Date of Patent: *Dec. 14, 2021

(54) METHOD OF MANUFACTURING MULTI-ANALYTE MICROSENSOR WITH MICRONEEDLES

(71) Applicant: One Drop Biosensor Technologies, LLC, New York, NY (US)

(72) Inventors: Ashwin Pushpala, San Francisco, CA (US); Alan Szmodis, San Francisco, CA (US); Matthew Chapman, San Francisco, CA (US); Weldon Hall, San Francisco, CA (US); Scott Miller, San Francisco, CA (US); Hooman Hafezi, San Francisco, CA (US)

(73) Assignee: One Drop Biosensor Technologies, LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/125,999

(22) Filed: Dec. 17, 2020

(65) Prior Publication Data
US 2021/0100505 A1 Apr. 8, 2021

Related U.S. Application Data

(63) Continuation of application No. 16/886,742, filed on May 28, 2020, which is a continuation of application
(Continued)

(51) Int. Cl.
*A61M 37/00* (2006.01)
*G01N 27/327* (2006.01)
(Continued)

(52) U.S. Cl.
CPC ....... *A61M 37/0015* (2013.01); *A61B 5/1495* (2013.01); *A61B 5/14503* (2013.01);
(Continued)

(58) Field of Classification Search
None
See application file for complete search history.

(56) References Cited

U.S. PATENT DOCUMENTS

| | | | |
|---|---|---|---|
| 4,953,552 A | 9/1990 | DeMarzo | |
| 5,215,088 A * | 6/1993 | Normann | ............... A61B 5/685 600/377 |

(Continued)

FOREIGN PATENT DOCUMENTS

| | | |
|---|---|---|
| CN | 1735375 A | 2/2006 |
| CN | 102469941 A | 5/2012 |

(Continued)

OTHER PUBLICATIONS

Baron et al. "Investigations of development process of high hollowed beveled microneedles using a combination of ICP RIE and dicing saw" Microsys. Technology, 2008. Vo. 14 pp. 1475-1480. (Year: 2008).*

(Continued)

*Primary Examiner* — Cachet I Proctor
(74) *Attorney, Agent, or Firm* — Perkins Coie LLP

(57) ABSTRACT

A microsensor and method of manufacture for a microsensor, comprising an array of filaments, wherein each filament of the array of filaments comprises a substrate and a conductive layer coupled to the substrate and configured to facilitate analyte detection. Each filament of the array of filaments can further comprise an insulating layer configured to isolate regions defined by the conductive layer for analyte detection, a sensing layer coupled to the conductive layer, configured to enable transduction of an ionic concentration to an electronic voltage, and a selective coating coupled to the sensing layer, configured to facilitate detection of specific target analytes/ions. The microsensor facilitates detec-
(Continued)

tion of at least one analyte present in a body fluid of a user interfacing with the microsensor.

30 Claims, 15 Drawing Sheets

Related U.S. Application Data

No. 16/722,977, filed on Dec. 20, 2019, which is a continuation of application No. 14/876,692, filed on Oct. 6, 2015, now Pat. No. 10,549,080, which is a continuation of application No. 14/211,404, filed on Mar. 14, 2014, now Pat. No. 9,182,368.

(60) Provisional application No. 61/905,583, filed on Nov. 18, 2013, provisional application No. 61/781,754, filed on Mar. 14, 2013.

(51) Int. Cl.
    *A61B 5/15*       (2006.01)
    *A61B 5/00*       (2006.01)
    *A61B 5/145*      (2006.01)
    *A61B 5/1486*     (2006.01)
    *A61B 5/1495*     (2006.01)
    *C12Q 1/00*       (2006.01)
    *A61M 25/00*      (2006.01)

(52) U.S. Cl.
    CPC ...... *A61B 5/14514* (2013.01); *A61B 5/14532* (2013.01); *A61B 5/14546* (2013.01); *A61B 5/14865* (2013.01); *A61B 5/150022* (2013.01); *A61B 5/150282* (2013.01); *A61B 5/150427* (2013.01); *A61B 5/150969* (2013.01); *A61B 5/150984* (2013.01); *A61B 5/4839* (2013.01); *A61B 5/685* (2013.01); *C12Q 1/006* (2013.01); *G01N 27/3271* (2013.01); *A61B 2562/028* (2013.01); *A61B 2562/12* (2013.01); *A61B 2562/125* (2013.01); *A61M 25/00* (2013.01); *A61M 2037/0023* (2013.01); *A61M 2037/0046* (2013.01); *A61M 2037/0053* (2013.01); *Y10T 29/49117* (2015.01)

(56) References Cited

U.S. PATENT DOCUMENTS

| | | | |
|---|---|---|---|
| 5,863,833 A | 1/1999 | Shin | |
| 5,949,739 A | 9/1999 | Reese | |
| 6,001,067 A | 12/1999 | Shults et al. | |
| 6,083,196 A * | 7/2000 | Trautman | A61M 37/0015 604/46 |
| 6,091,975 A | 7/2000 | Daddona et al. | |
| 6,275,717 B1 | 8/2001 | Gross et al. | |
| 6,424,847 B1 | 7/2002 | Mastrototaro et al. | |
| 6,451,240 B1 * | 9/2002 | Sherman | A61M 37/0015 205/164 |
| 6,501,976 B1 | 12/2002 | Sohrab | |
| 6,560,471 B1 | 5/2003 | Heller et al. | |
| 6,582,573 B2 | 6/2003 | Douglas et al. | |
| 6,619,093 B2 | 9/2003 | Dawson et al. | |
| 6,690,959 B2 | 2/2004 | Thompson | |
| 6,699,667 B2 | 3/2004 | Keen | |
| 6,743,211 B1 | 6/2004 | Prausnitz et al. | |
| 6,749,792 B2 | 6/2004 | Olson | |
| 6,790,179 B2 | 9/2004 | Skover | |
| 6,793,632 B2 | 9/2004 | Sohrab | |
| 6,837,988 B2 | 1/2005 | Leong et al. | |
| 6,863,833 B1 | 3/2005 | Bloom et al. | |
| 6,875,613 B2 | 4/2005 | Shartle et al. | |
| 6,923,764 B2 | 8/2005 | Aceti et al. | |
| 6,931,277 B1 | 8/2005 | Yuzhakov et al. | |
| 7,029,444 B2 | 4/2006 | Shin et al. | |
| 7,295,867 B2 | 11/2007 | Berner et al. | |
| 7,322,960 B2 | 1/2008 | Yamamoto et al. | |
| 7,361,307 B2 | 4/2008 | Shartle et al. | |
| 7,399,585 B2 | 7/2008 | Gau | |
| 7,585,278 B2 | 9/2009 | Aceti et al. | |
| 7,591,801 B2 | 9/2009 | Brauker et al. | |
| 7,732,002 B2 | 6/2010 | Kodas et al. | |
| 7,753,888 B2 | 7/2010 | Mukerjee et al. | |
| 7,783,442 B2 | 8/2010 | Mueller et al. | |
| 7,885,697 B2 | 2/2011 | Brister et al. | |
| 7,920,906 B2 | 4/2011 | Goode et al. | |
| 7,946,984 B2 | 5/2011 | Brister et al. | |
| 7,949,382 B2 | 5/2011 | Jina | |
| 7,951,300 B2 | 5/2011 | Bhandari et al. | |
| 8,080,385 B2 | 12/2011 | Heller et al. | |
| 8,114,269 B2 | 2/2012 | Cooper et al. | |
| 8,224,414 B2 | 7/2012 | Kellogg et al. | |
| 8,280,475 B2 | 10/2012 | Brister et al. | |
| 8,280,476 B2 | 10/2012 | Jina | |
| 8,290,559 B2 | 10/2012 | Shariati et al. | |
| 8,361,037 B2 | 1/2013 | Gonnelli | |
| 8,386,027 B2 | 2/2013 | Chuang et al. | |
| 8,478,557 B2 | 7/2013 | Hayter et al. | |
| 8,565,849 B2 | 10/2013 | Kamath et al. | |
| 8,604,810 B2 | 12/2013 | Sheppard | |
| 8,608,924 B2 | 12/2013 | Cooper et al. | |
| 8,615,282 B2 | 12/2013 | Brister et al. | |
| 8,641,672 B2 | 2/2014 | Yodfat et al. | |
| 8,663,106 B2 | 3/2014 | Stivoric et al. | |
| 8,668,645 B2 | 3/2014 | Drucker et al. | |
| 8,677,188 B2 | 3/2014 | Eickmeyer et al. | |
| 8,700,114 B2 | 4/2014 | Gottlieb et al. | |
| 8,718,742 B2 | 5/2014 | Beck et al. | |
| 8,734,348 B2 | 5/2014 | Say et al. | |
| 8,744,545 B2 | 6/2014 | Say et al. | |
| 8,744,547 B2 | 6/2014 | Budiman et al. | |
| 8,774,887 B2 | 7/2014 | Say et al. | |
| 8,792,953 B2 | 7/2014 | Brister et al. | |
| 8,808,532 B2 | 8/2014 | Yang et al. | |
| 8,858,912 B2 | 10/2014 | Boyden et al. | |
| 8,865,288 B2 | 10/2014 | Bhandari et al. | |
| 8,882,670 B2 | 11/2014 | Hancock | |
| 8,886,279 B2 * | 11/2014 | Tathireddy | A61N 1/0529 600/378 |
| 8,965,477 B2 | 2/2015 | Hoss et al. | |
| 9,008,745 B2 | 4/2015 | Pushpala et al. | |
| 9,011,332 B2 | 4/2015 | Heller et al. | |
| 9,044,199 B2 | 6/2015 | Brister et al. | |
| 9,055,901 B2 | 6/2015 | Brister et al. | |
| 9,182,368 B2 | 11/2015 | Pushpala et al. | |
| 9,192,328 B2 | 11/2015 | Brauker et al. | |
| 9,195,799 B2 | 11/2015 | Sze et al. | |
| 9,215,995 B2 | 12/2015 | Gottlieb et al. | |
| 9,220,483 B2 | 12/2015 | Frankhouser et al. | |
| 9,278,174 B2 | 3/2016 | Gray | |
| 9,357,951 B2 | 6/2016 | Simpson et al. | |
| 9,387,000 B2 | 7/2016 | Corrie et al. | |
| 9,402,544 B2 | 8/2016 | Yee et al. | |
| 9,414,777 B2 | 8/2016 | Brister et al. | |
| 9,474,478 B2 | 10/2016 | Bhavaraju et al. | |
| 9,498,159 B2 | 11/2016 | Heller et al. | |
| 9,504,411 B2 | 11/2016 | Engelhardt et al. | |
| 9,532,741 B2 | 1/2017 | Brauker et al. | |
| 9,603,557 B2 | 3/2017 | Brister et al. | |
| 9,615,851 B2 | 4/2017 | Neinast et al. | |
| 9,632,060 B2 | 4/2017 | Shah et al. | |
| 9,662,047 B2 | 5/2017 | Barman et al. | |
| 9,675,790 B2 * | 6/2017 | Stoeber | B21G 1/00 |
| 9,737,247 B2 | 8/2017 | Wang et al. | |
| 9,743,870 B2 | 8/2017 | Wang et al. | |
| 9,814,389 B2 | 11/2017 | DeHennis | |
| 9,974,471 B1 | 5/2018 | Kam et al. | |
| 10,046,114 B1 | 8/2018 | Biederman et al. | |
| 10,070,820 B2 | 9/2018 | Huang | |
| 10,136,846 B2 | 11/2018 | Wang et al. | |
| 10,173,042 B2 | 1/2019 | Pushpala et al. | |
| 10,238,289 B2 | 3/2019 | Hagi | |
| 10,321,858 B2 | 6/2019 | Maiz-Aguinaga et al. | |

(56) References Cited

U.S. PATENT DOCUMENTS

| | | | |
|---|---|---|---|
| 10,327,678 B2 | 6/2019 | Gottlieb et al. | |
| 10,383,558 B2 | 8/2019 | Cho et al. | |
| 10,524,730 B2 | 1/2020 | Reitz et al. | |
| 10,549,080 B2 | 2/2020 | Pushpala et al. | |
| 10,667,733 B2 | 6/2020 | Simpson et al. | |
| 10,765,369 B2 | 9/2020 | Antonio et al. | |
| 10,799,158 B2 | 10/2020 | Brister et al. | |
| 10,799,159 B2 | 10/2020 | Brister et al. | |
| 10,806,384 B2 | 10/2020 | Frey et al. | |
| 10,813,577 B2 | 10/2020 | Brister et al. | |
| 10,820,860 B2 | 11/2020 | Pushpala et al. | |
| 10,827,954 B2 | 11/2020 | Hoss et al. | |
| 10,835,161 B2 | 11/2020 | Simpson et al. | |
| 10,874,335 B2 | 12/2020 | Cho et al. | |
| 2002/0015963 A1 | 2/2002 | Keen | |
| 2002/0062202 A1 | 5/2002 | Arai | |
| 2002/0082543 A1* | 6/2002 | Park | A61N 1/30 604/21 |
| 2002/0123048 A1 | 9/2002 | Gau | |
| 2002/0168290 A1* | 11/2002 | Yuzhakov | A61B 5/15117 422/400 |
| 2003/0100821 A1 | 5/2003 | Heller et al. | |
| 2004/0060902 A1 | 4/2004 | Evans et al. | |
| 2004/0260241 A1 | 12/2004 | Yamamoto et al. | |
| 2005/0004438 A1 | 1/2005 | Ward et al. | |
| 2005/0245839 A1 | 11/2005 | Stivoric et al. | |
| 2006/0015058 A1 | 1/2006 | Kellogg et al. | |
| 2006/0016700 A1 | 1/2006 | Brister et al. | |
| 2006/0258929 A1 | 11/2006 | Goode et al. | |
| 2006/0264716 A1* | 11/2006 | Zander | A61B 5/14865 600/309 |
| 2007/0032717 A1 | 2/2007 | Brister et al. | |
| 2007/0179371 A1 | 8/2007 | Peyser et al. | |
| 2007/0208245 A1 | 9/2007 | Brauker et al. | |
| 2007/0219480 A1 | 9/2007 | Kamen et al. | |
| 2008/0033254 A1 | 2/2008 | Kamath et al. | |
| 2008/0045825 A1* | 2/2008 | Melker | A61B 5/1486 600/365 |
| 2008/0058726 A1 | 3/2008 | Jina et al. | |
| 2008/0138582 A1 | 6/2008 | Bhandari et al. | |
| 2008/0154107 A1 | 6/2008 | Jina | |
| 2008/0213461 A1* | 9/2008 | Gill | A61K 9/0021 427/2.3 |
| 2008/0275400 A1* | 11/2008 | Ferguson | B29C 45/561 604/173 |
| 2008/0307849 A1* | 12/2008 | Lim | A61M 37/0015 72/355.4 |
| 2008/0319285 A1 | 12/2008 | Hancock | |
| 2008/0319298 A1 | 12/2008 | Huys et al. | |
| 2009/0099502 A1 | 4/2009 | Tokumoto et al. | |
| 2009/0156924 A1 | 6/2009 | Shariati et al. | |
| 2009/0234301 A1* | 9/2009 | Tomono | B29C 43/021 604/272 |
| 2009/0259118 A1 | 10/2009 | Feldman et al. | |
| 2009/0294307 A1 | 12/2009 | Liu et al. | |
| 2009/0301994 A1* | 12/2009 | Bhandari | A61B 5/685 216/11 |
| 2009/0321277 A1 | 12/2009 | Heller et al. | |
| 2010/0010601 A1 | 1/2010 | Negi et al. | |
| 2010/0016687 A1 | 1/2010 | Brauker et al. | |
| 2010/0030045 A1 | 2/2010 | Gottlieb et al. | |
| 2010/0075353 A1 | 3/2010 | Heaton | |
| 2010/0112195 A1 | 5/2010 | Kodas et al. | |
| 2010/0113897 A1 | 5/2010 | Brenneman et al. | |
| 2010/0152651 A1 | 6/2010 | Boyden et al. | |
| 2010/0298895 A1 | 11/2010 | Ghaffari et al. | |
| 2010/0324392 A1 | 12/2010 | Yee et al. | |
| 2011/0009824 A1 | 1/2011 | Yodfat et al. | |
| 2011/0029269 A1 | 2/2011 | Hayter et al. | |
| 2011/0053121 A1 | 3/2011 | Heaton | |
| 2011/0089957 A1 | 4/2011 | Sheppard | |
| 2011/0125058 A1 | 5/2011 | Levinson et al. | |
| 2011/0224515 A1* | 9/2011 | Mir | A61B 5/150435 600/317 |
| 2011/0237917 A1 | 9/2011 | Roy et al. | |
| 2011/0237925 A1 | 9/2011 | Yue et al. | |
| 2011/0257495 A1 | 10/2011 | Hoss et al. | |
| 2011/0319734 A1 | 12/2011 | Gottlieb et al. | |
| 2012/0035442 A1 | 2/2012 | Barman et al. | |
| 2012/0046533 A1* | 2/2012 | Voskanyan | A61B 5/14532 600/347 |
| 2012/0078071 A1 | 3/2012 | Bohm et al. | |
| 2012/0108931 A1 | 5/2012 | Taub et al. | |
| 2012/0165639 A1 | 6/2012 | Engelhardt et al. | |
| 2012/0190950 A1 | 7/2012 | Yang et al. | |
| 2012/0190952 A1 | 7/2012 | Stafford | |
| 2012/0203078 A1 | 8/2012 | Sze et al. | |
| 2012/0209244 A1 | 8/2012 | Gray | |
| 2012/0209303 A1 | 8/2012 | Frankhouser et al. | |
| 2012/0215087 A1 | 8/2012 | Cobelli et al. | |
| 2012/0238841 A1 | 9/2012 | Castle et al. | |
| 2012/0265034 A1 | 10/2012 | Wisniewski et al. | |
| 2012/0265042 A1 | 10/2012 | Neinast et al. | |
| 2013/0178726 A1 | 7/2013 | Wang et al. | |
| 2013/0190583 A1 | 7/2013 | Grosman et al. | |
| 2013/0225956 A1 | 8/2013 | Huang et al. | |
| 2013/0248364 A1 | 9/2013 | Kahn et al. | |
| 2013/0267811 A1 | 10/2013 | Pryor et al. | |
| 2013/0310665 A1 | 11/2013 | Crean et al. | |
| 2013/0328578 A1 | 12/2013 | Shah et al. | |
| 2013/0331676 A1 | 12/2013 | Morgan et al. | |
| 2013/0338598 A1 | 12/2013 | Gyrn | |
| 2013/0338632 A1* | 12/2013 | Kaplan | A61P 43/00 604/506 |
| 2014/0012510 A1 | 1/2014 | Mensinger et al. | |
| 2014/0066735 A1 | 3/2014 | Engelhardt et al. | |
| 2014/0275897 A1 | 9/2014 | Pushpala et al. | |
| 2014/0336487 A1* | 11/2014 | Wang | A61B 5/1473 600/352 |
| 2016/0038180 A1 | 2/2016 | Kube et al. | |
| 2017/0128009 A1 | 5/2017 | Pushpala et al. | |
| 2020/0121902 A1 | 4/2020 | Pushpala et al. | |
| 2020/0390395 A1 | 12/2020 | Pushpala et al. | |
| 2020/0405234 A1 | 12/2020 | Pushpala et al. | |
| 2021/0100504 A1 | 4/2021 | Pushpala et al. | |

FOREIGN PATENT DOCUMENTS

| | | |
|---|---|---|
| CN | 103458810 A | 12/2013 |
| EP | 1266608 B1 | 8/2006 |
| EP | 2327362 A1 | 6/2011 |
| JP | 4112499 B2 | 7/2008 |
| JP | 4373604 B2 | 11/2009 |
| JP | 4439733 B2 | 3/2010 |
| JP | 4574847 B2 | 11/2010 |
| JP | 4905906 B2 | 3/2012 |
| JP | 5021115 B2 | 9/2012 |
| JP | 2013502978 A | 1/2013 |
| JP | 5591715 B2 | 9/2014 |
| JP | 5640110 B2 | 12/2014 |
| JP | 2015505251 A | 2/2015 |
| JP | 5680960 B2 | 3/2015 |
| JP | 5749751 B2 | 7/2015 |
| JP | 5795584 B2 | 10/2015 |
| JP | 2016508763 A | 3/2016 |
| JP | 2016518881 A | 6/2016 |
| JP | 2016517601 A | 4/2017 |
| WO | 1994020602 A1 | 9/1994 |
| WO | 1999019507 A1 | 4/1999 |
| WO | 1999045375 A1 | 9/1999 |
| WO | 1999045387 A2 | 9/1999 |
| WO | 1999056613 A1 | 11/1999 |
| WO | 1999058709 A1 | 11/1999 |
| WO | 2000074763 A2 | 12/2000 |
| WO | 2002058537 A2 | 8/2002 |
| WO | 2002062202 A2 | 8/2002 |
| WO | 2002097414 A2 | 12/2002 |
| WO | 2003085372 A2 | 10/2003 |
| WO | 2008028087 A2 | 3/2008 |
| WO | 2008157820 A1 | 12/2008 |
| WO | 2009082699 A1 | 7/2009 |
| WO | 2009105145 A1 | 8/2009 |
| WO | 2011025549 A1 | 3/2011 |

(56) References Cited

FOREIGN PATENT DOCUMENTS

| WO | 2013058879 A2 | 4/2013 |
| WO | 2013070794 A2 | 5/2013 |
| WO | 2013163035 A1 | 10/2013 |
| WO | 2014106263 A2 | 7/2014 |
| WO | 2014145001 A1 | 9/2014 |
| WO | 2014145049 A2 | 9/2014 |

OTHER PUBLICATIONS

U.S. Appl. No. 16/722,977, filed Dec. 20, 2019, On-Body Microsensor for Biomonitoring.

U.S. Appl. No. 16/886,742, filed May 28, 2020, Method of Manufacturing Multi-Analyte Microsensor With Microneedles.

U.S. Appl. No. 17/125,992, filed Dec. 17, 2020, Method of Manufacturing Multi-Analyte Microsensor With Microneedles.

U.S. Appl. No. 16/942,645, filed Jul. 29, 2020, On-Body Microsensor for Biomonitoring.

Adhikari, Basudam, et al., "Polymers in sensor applications", Prog. Polym. Sci. vol. 29, pp. 699-766, Jan. 1, 2004.

Baron et al. "Investigations of development process of high hollow beveled microneedles using a combination of ICP RIE and dicing saw" Microsys. Technol., 2008, vol. 14, pp. 1475-1480.

Bhandari et al. "Wafer-scale fabrication of penetrating neuralmicroelectrode arrays" Biomed Microdevices, 2010, vol. 12, pp. 797-807.

CNIPA, Office Action Received for Chinese Patent Application No. 2014800271779, dated Feb. 2, 2017.

CNIPA, Office Action received for Chinese Patent Application No. 2015800127310, dated Jul. 24, 2018.

EPO, Examination Report for European Patent Application No. 15762313.3, dated Mar. 20, 2019. 6 pages.

EPO, Extended European Search Report for European Patent Application No. 15762313.3, dated Sep. 29, 2017. 9 pages.

EPO, Office Action received for European Patent Application No. 14770855.6, dated Nov. 25, 2016.

ISA, International Search Report and Written Opinion for International Patent Application No. PCT/US2014/027655, dated Sep. 5, 2014. 10 pages.

ISA, International Search Report and Written Opinion for International Patent Application No. PCT/US2015/020586, dated Jun. 24, 2015. 9 pages.

* cited by examiner

Vertex-aligned Tip          Centered Tip

Array

METHOD OF MANUFACTURING MULTI-ANALYTE MICROSENSOR WITH MICRONEEDLES

CROSS REFERENCE TO RELATED APPLICATIONS

This application is a continuation of U.S. application Ser. No. 16/886,742, filed May 28, 2020 (U.S. Pat. No. 11,123,532), which is a continuation of U.S. application Ser. No. 16/722,977, filed Dec. 20, 2019, which is a continuation of U.S. application Ser. No. 14/876,692, filed Oct. 6, 2015 (U.S. Pat. No. 10,549,080), which is a continuation of U.S. application Ser. No. 14/211,404, filed Mar. 14, 2014 (U.S. Pat. No. 9,182,368), which claims priority to U.S. Provisional Application No. 61/905,583, filed Nov. 18, 2013 and U.S. Provisional Application No. 61/781,754, filed Mar. 14, 2013, all of the aforementioned applications are herein incorporated by reference in their entireties.

TECHNICAL FIELD

This invention relates generally to the medical device field, and more specifically to a new and useful on-body multi-analyte microsensor for biomonitoring.

BACKGROUND

Biomonitoring devices are commonly used, particularly by health-conscious individuals and individuals diagnosed with ailments, to monitor body chemistry. Conventional biomonitoring devices typically include analysis and display elements. Such biomonitoring devices perform the tasks of determining one or more vital signs characterizing a physiological state of a user, and provide information regarding the user's physiological state to the user. In variations, biomonitoring devices can determine an analyte level present in a user's body, and provide information regarding the analyte level to the user; however, these current biomonitoring devices typically convey information to users that is limited in detail, intermittent, and prompted by the command of the user. Such biomonitoring devices, including blood glucose meters, are also inappropriate for many applications outside of intermittent use, due to design and manufacture considerations. Additionally current devices are configured to analyze one or a limited number of analytes contributing to overall body chemistry, due to limitations of sensors used in current biomonitoring devices.

There is thus a need in the medical device field to create a new and useful on-body microsensor for biomonitoring. This invention provides such a new and useful microsensor.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Microsensor

Figure 1A:
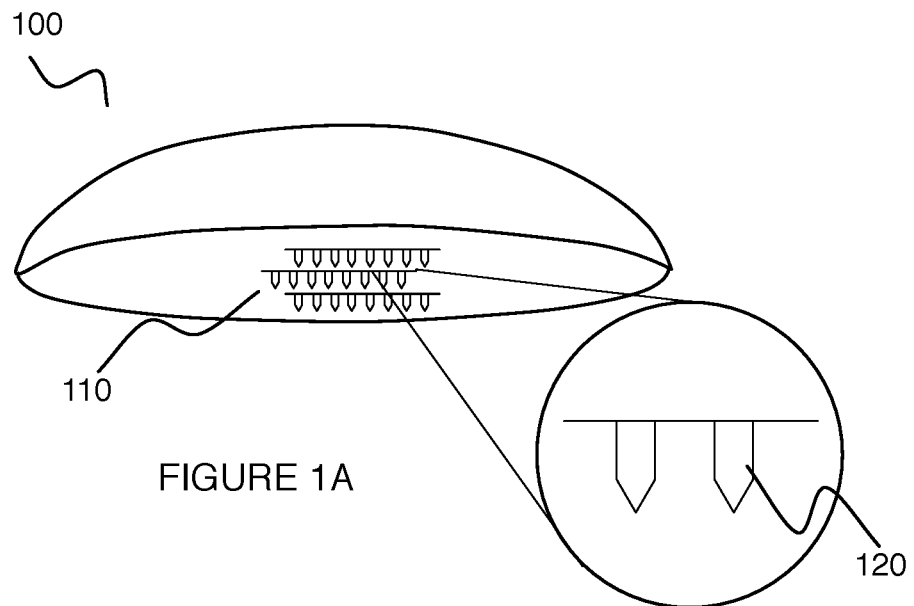
FIG. 1A depicts an embodiment of a microsensor for biomonitoring.
Figure 2A:
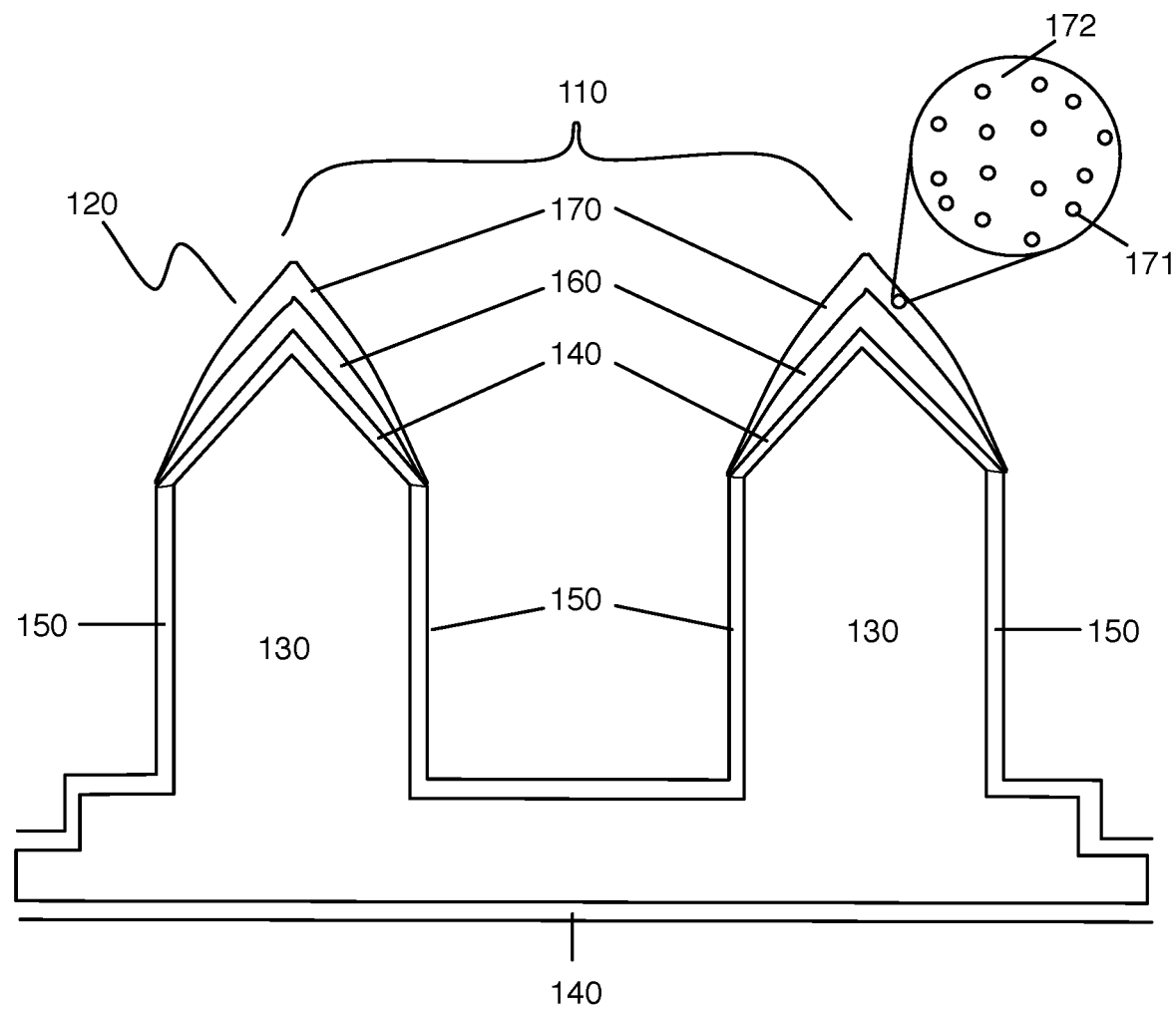
FIG. 2A depicts an embodiment of a filament for biomonitoring.
Figure 2B:
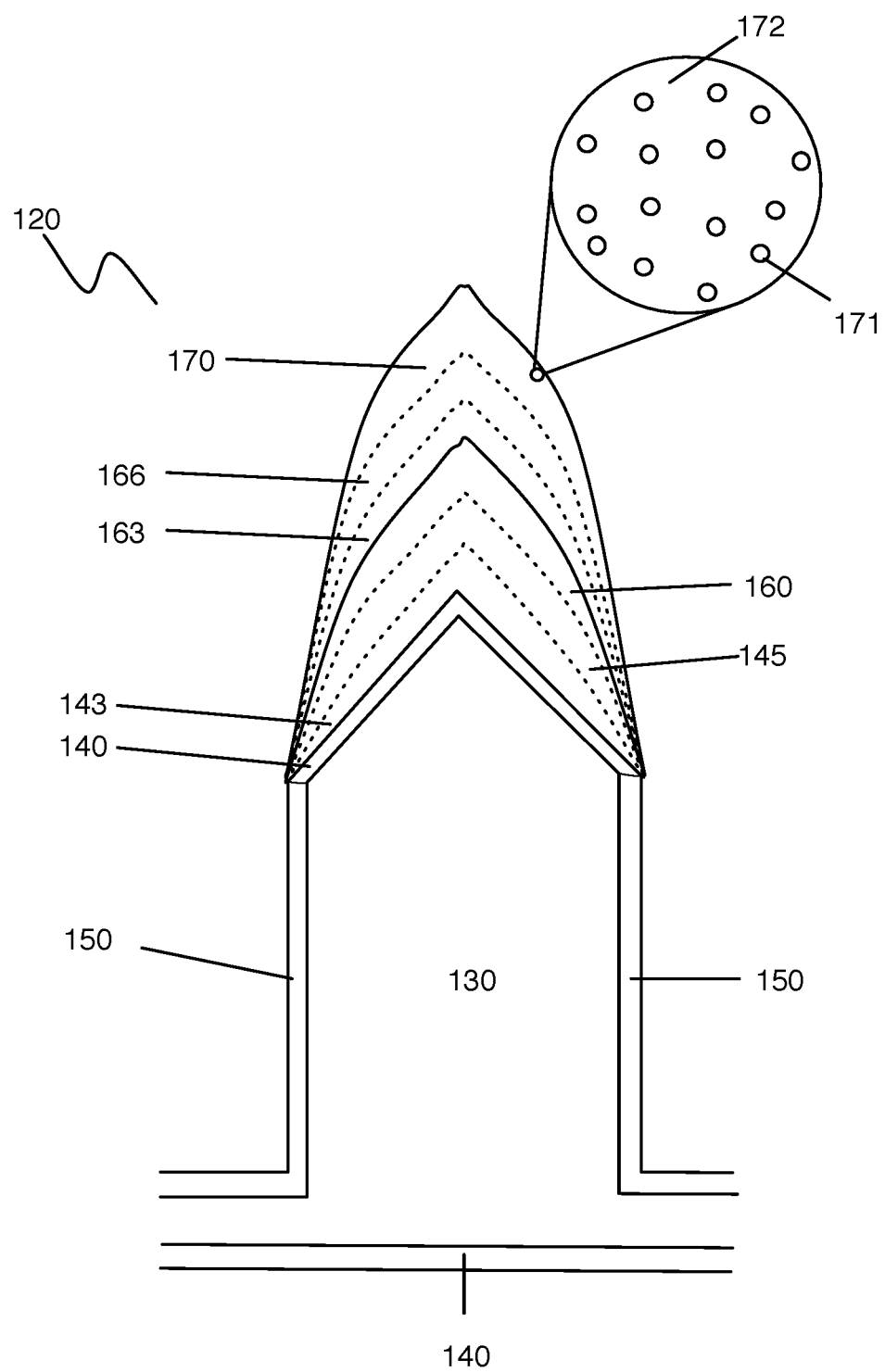
FIG. 2B depicts another embodiment of a filament for biomonitoring.

As shown in FIGS. 1A, 2A, and 2B, an embodiment of a microsensor 100 comprises an array of filaments 110, wherein each filament 120 of the array of filaments 110 comprises a substrate 130 and a conductive layer 140 configured to facilitate analyte detection. Alternatively, the substrate 130 itself can be conductive with no additional conductive layer 140. Each filament 120 of the array of filaments 110 can further comprise an insulating layer 150 configured to isolate regions for analyte detection, a sensing layer 160 configured to enable transduction of an ionic concentration to an electronic voltage, and a selective coating 170 configured to facilitate detection of specific target analytes/ions. Any filament 120 of the array of filaments 110 can further comprise an adhesion coating 180 configured to maintain contact between layers, coatings, and/or substrates of the filament 120, and a temporary functional layer 190 configured to facilitate penetration of a filament into the body. The microsensor 100 and the array of filaments 110 thus function to penetrate a user's skin in order to sense at least one target analyte characterizing the user's body chemistry. Preferably, the microsensor 100 is configured to be worn by a user, such that continuous or semi-continuous monitoring of the user's body chemistry is enabled; however, the microsensor 100 can alternatively be used intermittently to sense analytes characterizing the user's body chemistry. Preferably, the microsensor 100 is configured to penetrate the user's stratum corneum (e.g., an outer skin layer) in order to sense analytes characterizing the user's body chemistry in the user's interstitial (extracellular) fluid; however, the microsensor 100 can alternatively be configured to penetrate deeper layers of a user's skin in order to sense analytes within any appropriate bodily fluid of the user, such as the user's blood. The microsensor 100 can be configured to sense analytes/ions characterizing a user's body chemistry using a potentiometric measurement (e.g., for analytes including potassium, sodium calcium, alcohol, cortisol, hormones, etc.), using an amperometric measurement (e.g., for analytes including glucose, lactic acid, creatinine, etc.), using a conductometric measurement, or using any other suitable measurement.

Figure 1B:
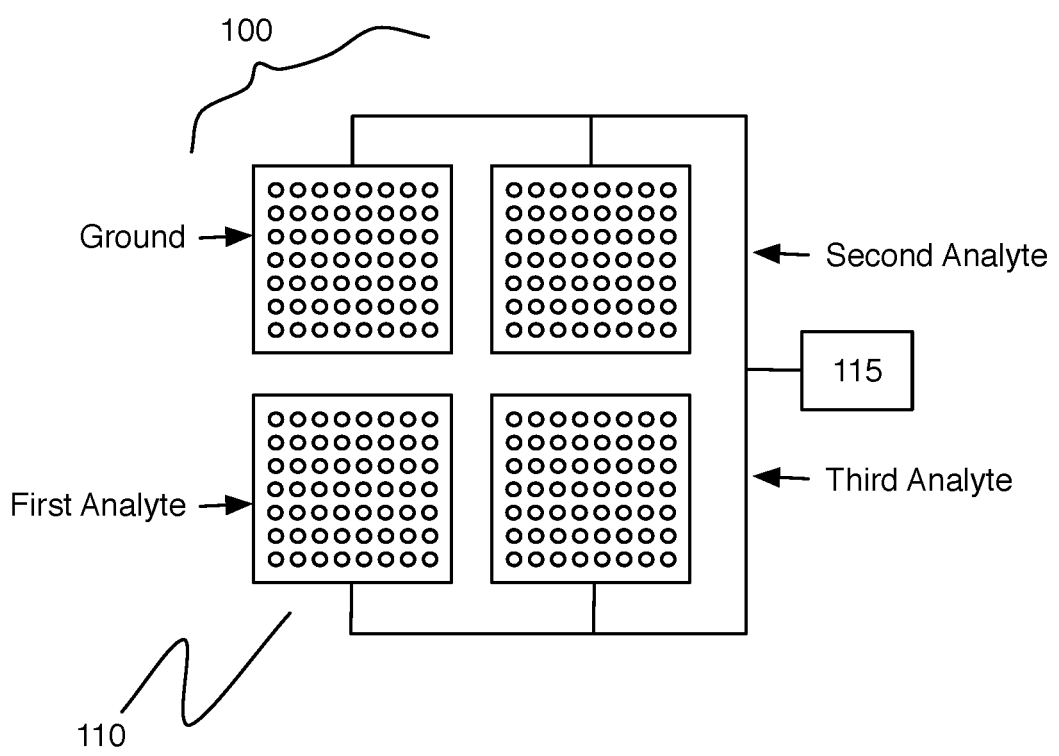
FIG. 1B depicts an embodiment of an array of filaments, and a microsensor coupled to an electronics module.

As shown in FIG. 1B, the microsensor 100 can also be coupled to an electronics module 115, such that sensed analytes result in a signal (e.g., voltage, current, resistance, capacitance, impedance, gravimetric, etc.) detectable by the electronics module 115; however, analyte sensing can comprise any other appropriate mechanism using the microsensor 100. In an embodiment wherein the microsensor 100 is coupled with an electronics module 115, the microsensor 100 can also be integrated with the electronics module 115, in variations wherein the electronics module 115 is characterized by semiconductor architecture. In a first variation, the microsensor 100 is coupled to the semiconductor architecture of the electronics module 115 (e.g., the microsensor 100 is coupled to an integrated circuit comprising the electronics module 115), in a second variation, the microsensor 100 is more closely integrated into the semiconductor architecture of the electronics module 115 (e.g., there is closer integration between the microsensor 100 and an integrated circuit including the electronics module 115), and in a third variation, the microsensor 100 and the electronics module 115 are constructed in a system-on-a-chip fashion (e.g., all components are integrated into a single chip). As such, in some variations, filaments 120 the array of filaments 110 of the microsensor 100 can be directly or indirectly integrated with electronics components, such that preprocessing of a signal from the microsensor 100 can be performed using the electronics components (e.g., of the filaments 120, of the electronics module 115) prior to or after transmitting signals to the electronics module 115 (e.g., to an analog to digital converter). The electronics components can be coupled to a filament substrate, or otherwise integrated with the filaments in any suitable fashion (e.g., wired, using a contact pad, etc.). Alternatively, the electronics components can be fully integrated into the electronics module 115 and configured to communicate with the microsensor 100, or the electronics components can be split between the microsensor and the electronics module 115. The microsensor 100 can, however, comprise any other suitable architecture or configuration.

The microsensor 100 preferably senses analyte parameters using the array of filaments 110, such that absolute values of specific analyte parameters can be detected and analyzed. The microsensor 100 can additionally or alternatively be configured to sense analyte parameters using the array of filaments 110, such that changes in values characterizing specific analyte parameters or derivatives thereof (e.g., trends in values of a parameter, slopes of curves characterizing a trend in a parameter vs. another parameter, areas under curves characterizing a trend, a duration of time spent within a certain parameter range, etc.) can be detected and analyzed. In one variation, sensing by the microsensor 100 is achieved at discrete time points (e.g., every minute or every hour), and in another variation, sensing by the microsensor 100 is achieved substantially continuously. Furthermore, sensing can be achieved continuously, with signal transmission performed in a discrete or non-discrete manner (e.g., prior to or subsequent to processing of a signal). In one specific example for blood chemistry analysis, the array of filaments 110 of the microsensor 100 is configured to sense at least one of electrolytes, glucose, bicarbonate, creatinine, blood urea nitrogen (BUN), sodium, and potassium of a user's body chemistry. In another specific example, the array of filaments 110 of the microsensor 100 is configured to sense at least one of biomarkers, cell count, hormone levels, alcohol content, gases, drug concentrations/ metabolism, pH and analytes within a user's body fluid.

1.1 Microsensor—Array of Filaments

The array of filaments 110 functions to interface directly with a user in a transdermal manner in order to sense at least one analyte characterizing the user's body chemistry. The array of filaments can be an array of fibers, an array of pillars, an array of microneedles, and/or any other suitable array configured to facilitate analyte detection in a user. The array of filaments 110 is preferably arranged in a uniform pattern with a specified density optimized to effectively penetrate a user's skin and provide an appropriate signal, while minimizing pain to the user. However, the array of filaments no can additionally or alternatively be coupled to the user in any other suitable manner (e.g., using an adhesive, using a coupling band/strap, etc.). Additionally, the array of filaments no can be arranged in a manner to optimize coupling to the user, such that the microsensor 100 firmly couples to the user over the lifetime usage of the microsensor 100. For example, the filaments 120 can comprise several pieces and/or be attached to a flexible base to allow the array of filaments no to conform to a user's body. In one variation, the array of filaments no is arranged in a rectangular pattern, and in another variation, the array of filaments no is arranged in a circular or ellipsoid pattern. However, in other variations, the array of filaments no can be arranged in any other suitable manner (e.g., a random arrangement). The array of filaments 110 can also be configured to facilitate coupling to a user, by comprising filaments of different lengths or geometries. Having filaments 120 of different lengths can additionally or alternatively function to allow measurement of different ions/analytes at different depths of penetration (e.g., a filament with a first length may sense one analyte at a first depth, and a filament with a second length may sense another analyte at a second depth). The array of filaments 110 can also comprise filaments 120 of different geometries (e.g., height, diameter) to facilitate sensing of analytes/ions at lower or higher concentrations. In one specific example, the array of filaments 110 is arranged at a density of 100 filaments per square centimeter and each filament 120 in the array of filaments no has a length of 250-350 microns, which allows appropriate levels of detection, coupling to a user, and comfort experienced by the user. In variations of the specific example, a filament 120 in the array of filaments 120 can have a length from 0-1000 m., or more specifically, a length from 150-500 µm.

Each filament 120 in the array of filaments no preferably functions to sense a single analyte; however, each filament 120 in the array of filaments no can additionally be configured to sense more than one analyte. Furthermore, the array of filaments no can be further configured, such that a subarray of the array of filaments 110 functions as a single sensor configured to sense a particular analyte or biomarker. As shown in FIG. 1B, multiple subarrays of the array of filaments 110 may then be configured to sense different analytes/biomarkers, or the same analyte/biomarker. Furthermore, a subarray or a single filament 120 of the array of filaments 110 can be configured as a ground region of the microsensor 100, such that signals generated by the microsensor 100 in response to analyte detection can be normalized by the signals generated by the subarray or single filament 120 serving as a ground region. Preferably, all subarrays of the array of filaments 110 are substantially equal in size and density; however, each subarray of the array of filaments 110 can alternatively be optimized to maximize signal generation and detection in response to a specific analyte. In an example, analytes that are known to have a lower concentration within a user's body fluid (e.g., interstitial fluid, blood) can correspond to a larger subarray of the array of filaments 110. In another example, analytes that are known to have a lower concentration within a user's body fluid can correspond to a smaller subarray of the array of filaments 110. In one extreme example, an entire array of filaments can be configured to sense a single analyte, such that the microsensor 100 is configured to sense and detect only one analyte.

In other variations, a subarray of the array of filaments 117 can also be used to detect other physiologically relevant parameters, including one or more of: electrophysiological signals (e.g., electrocardiogram, electroencephalogram), body temperature, respiration, heart rate, heart rate variability, galvanic skin response, skin impedance change (e.g., to measure hydration state or inflammatory response), and any other suitable biometric parameter. In these other variations, the subarray would be dedicated to measuring these physiologically relevant parameters, which could be combined with analyte/ion parameter measurements in order to provide meaningful information to a user. As an example, the simultaneous measurement of potassium levels and electrocardiogram measurements, enabled by subarrays of the array of filaments 117, may provide a more complete diagnosis of cardiovascular problems or events than either measurement by itself.

1.2 Microsensor—Filament

As shown in FIG. 2A, each filament 120 of the array of filaments 110 comprises a substrate 130 and a conductive layer 140 configured to facilitate analyte detection. Each filament 120 of the array of filaments 110 can further comprise an insulating layer 150 configured to isolate regions for analyte detection, a sensing layer 160 configured to enable transduction of an ionic concentration to an electronic voltage, and a selective coating 170 configured to facilitate detection of specific target analytes. As shown in FIG. 2E, each filament can further comprise an adhesion coating 180 configured to maintain contact between layers, coatings, and/or substrates of the filament 120, and/or a temporary functional layer 190, as shown in FIG. 2F, configured to facilitate penetration of a filament 120 into the body. A filament 120 thus functions to directly penetrate a user's skin, and to sense specific target analytes/ions characterizing the user's body chemistry.

The substrate 130 functions to provide a core or base structure upon which other layers or coatings can be applied, in order to facilitate processing of each filament 120 for specific functionalities. As such, the material of which the substrate 130 is composed can be processed to form at least one protrusion as a substrate core for a filament 120, including a base end coupled to the substrate 130 bulk and a tip at the distal end of the substrate core, that facilitates access to a body fluid of the user. Alternatively, the substrate 130 can be coupled to a protrusion (e.g., as a piece separate from the substrate) or a protrusion can be grown from a surface of the substrate 130 in any other suitable manner. Preferably, the material of the substrate 130 is processable to form an array of protrusions as substrate cores for the array of filaments 110; however, the material of the substrate 130 can alternatively be processable in any other suitable manner to form any other suitable filament structure. Preferably, the substrate 130 has a uniform composition; however, the substrate 130 can alternatively have a non-uniform composition comprising regions or layers configured to facilitate processing of subsequent functional layer/coating additions. The substrate 130 can be composed of a semiconducting material (e.g., silicon, quartz, gallium arsenide), a conducting material (e.g., gold, steel, platinum, nickel, silver, polymer, etc.), and/or an insulating or non-conductive material (e.g., glass, ceramic, polymer, etc.). In some variations, the substrate 130 can comprise a combination of materials (e.g., as in a composite, as in an alloy). Furthermore, in variations wherein the substrate 130 is non-conductive, a fluid path defined at the substrate 130 (e.g., a fluid channel, a groove, a hollow region, an outer region, etc.) and coupled to a conductive layer 140 (e.g., a conductive base region, a conductive core, a conductive outer layer) can enable signal transmission upon detection of an analyte/analyte concentration. In a specific example, the substrate 130 is composed of P-type, boron-doped, <100> orientation silicon with a resistivity of 0.005-0.01 ohm-cm, a thickness from 500-1500 μm, a total thickness variation (TTV) of <10 μm, with a first surface side polish. In variations of the specific example, the substrate 130 can be composed of silicon with any other suitable type, doping, miller index orientation, resistivity, thickness, TTV, and/or polish. Furthermore, the substrate 130 can be processed using semiconductor processing methods, machining methods, manufacturing processes suited to a ductile substrate material, and/or manufacturing methods suited to a brittle material.

The conductive layer 140 functions to provide a conductive "active" region to facilitate signal transmission upon detection of an analyte by a filament 120. The conductive layer 140 can comprise a layer of a single material, or can alternatively comprise multiple materials (e.g., multiple layers of one or more materials). In variations, the conductive layer 140 can include any one or more of: a platinum-based material, an iridium-based material, a tungsten-based material, a titanium-based material, a gold-based material, a nickel-based material, and any other suitable conductive or semiconducting material (e.g., silicon, doped silicon). Furthermore, the layer(s) of the conductive layer 140 can be defined by any suitable thickness that allows signal transmission upon detection of an analyte by the filament 120. In a first specific example, the conductive layer 140 includes a 1000 Å thick platinum layer, a 10000 Å thick iridium layer, a 10000 Å thick tungsten layer, and a 100 Å thick titanium nitride layer. In a second specific example, the conductive layer 140 includes a 10000 Å thick platinum layer and a 100 Å thick titanium layer. In a third specific example, the conductive layer 140 includes a 10000 Å thick platinum layer and a 100 Å thick titanium nitride layer. In a fourth specific example, the conductive layer 140 includes a 10000 Å thick iridium layer and a 100 Å thick titanium nitride layer. In a fifth specific example, the conductive layer 140 includes a 10000 Å thick tungsten layer. In a sixth specific example, the conductive layer 140 includes one or more of: nickel, gold, and platinum (e.g., deposited by electroplating). Preferably, the conductive layer 140 only covers a portion of the substrate 130 (e.g., a substrate core) contacting the user's body fluids, thus forming an "active region" of the filament 120, and in one variation, covers a tip region of each filament 120 (e.g., a tip of a substrate core); however, the conductive layer 140 can alternatively cover the entire surface of the substrate 130 contacting a user's body fluids. In variations wherein the substrate 130 is conductive, the filament 120 can altogether omit the conductive layer 140. Furthermore, in variations wherein the substrate 130 is non-conductive, a fluid path defined at the substrate 130 (e.g., a fluid channel, a groove, a hollow region, an outer region, etc.) and coupled to a conductive layer 140 (e.g., a conductive base region, a conductive core, a conductive outer layer) can enable signal transmission upon detection of an analyte/analyte concentration, as described above.

The insulating layer 150 functions to form an insulating region of a filament 120, and is configured to provide a "non-active" region of the filament 120. Additionally, the insulating layer 150 functions to define and/or isolate an "active" region of the filament 120. As such, the insulating layer 150 preferably leaves at least a portion of the conductive layer 140 exposed to define the active region of the filament 120. In one variation, the insulating layer 150 ensheathes the substrate core of each filament 120 in the array of filaments, and can additionally or alternatively cover all exposed regions of the substrate 130 to isolate areas of signal transmission. The insulating layer 150 preferably includes an oxide layer that is grown at desired surfaces of the substrate (e.g., to a thickness of 0.1-10 m), thereby forming the insulating layer. However, the insulating layer 150 can additionally or alternatively include any other suitable material that is not removable during removal of sacrificial layers used during processing of the array of filaments 110. As such, in other variations, the insulating layer 150 can be composed of any one or more of: an insulating polymer (e.g., polyimide, cyanate ester, polyurethane, silicone) that is chemical and/or heat resistant, an oxide, a carbide, a nitride (e.g., of silicon, of titanium), and any other suitable insulating material. Preferably, the insulating layer 150 only covers a portion of the substrate contacting the user's body fluids, thus defining an "active region" of the filament 120 and a "non-active" region of the filament 120. Alternatively, the filament 120 can altogether omit the insulating layer 150.

The sensing layer 160 functions to enable transduction of an ionic concentration to an electronic voltage, to enable measurement of analyte/ion concentrations characterizing body chemistry. The sensing layer 160 can also function to prevent unwanted signal artifacts due to oxygen fluxes in a user's body fluids. Furthermore, the sensing layer 160 can also enable transduction of a molecular species concentration through a current, capacitance, or resistance change. Preferably, the sensing layer is a conductive material with reversible redox reaction behavior, such that detection of increased ion concentrations followed by decreased ion concentrations (or visa versa) can be enabled by the sensing layer 160. Additionally, the sensing layer 160 is preferably an appropriately bio-safe, anti-inflammatory, and anti-microbial material. The sensing layer 160 can be a polymer, such as polypyrrole or polyaniline, which undergoes a reversible redox reaction characterized by the following generic equation: $P^{(ox)} + e- \Leftrightarrow P^{(red)}$. The sensing layer 160 can additionally or alternatively be composed of any appropriate conductive material (e.g., sulfur-containing polythiophenes, silver chloride, etc.) that has reversible redox reaction behavior. For example, silver chloride undergoes a reversible redox reaction characterized by the following equation: $AgCl + e- \Leftrightarrow Ag(s)^+ + Cl^-$. In either example redox reaction equation, electron (e–) generation results in measurable signals corresponding to detected ion concentrations for analyte detection, and further, the sensing layer 160 serves as a reference electrode for ion concentration measurements based upon a detected voltage change across a selective coating 170 coupled to the sensing layer 160. However, in other variations, the sensing layer 160 may not comprise a material with reversible redox reaction behavior, and other variations can further comprise a controlled ion coating (e.g., poly-hydroxyl ethyl methacrylate prepared with potassium chloride) that functions to form a portion of a reference electrode for ion concentration measurements. Additionally or alternatively, the sensing layer 160 can include molecules (e.g., glucose oxidase, phenylenediamine, gluteraldehyde, lysine, tyramine, trehalose, lipids, surfactants, etc.) that facilitate analyte detection. In one example, the sensing layer 160 includes electropolymerized phenylenediamene, tyramine, glucose oxidase, and poly-lysine to facilitate glucose sensing. The sensing layer 160 is preferably uniform over an active region of a filament 120 defined by the conductive layer 140 and the insulating layer 150; however, the sensing layer 160 can alternatively non-discriminately coat the surface of the filament 120, and/or can be a non-uniform coating. The sensing layer 160 can be maintained at a viable state by packaging the microsensor 100 in a hydrated state; however, the sensing layer 160 can be alternatively be configured to equilibrate within a short time period (e.g., less than one hour) upon coupling of the array of filaments 110 to a user. Alternative variations of the filament may altogether omit the sensing layer 160.

The selective coating 170 functions to facilitate sensing of specific target analytes. The selective coating 170 preferably facilitates ion-selective reactions that generate signals reflective of ion concentration; however, the selective coating 170 can additionally or alternatively facilitate enzyme reactions that generate changes in signals (e.g., current) due to binding of complementary molecules to target analytes/ions. The selective coating 170 is preferably anti-microbial and anti-inflammatory, and can additionally or alternatively include any other features that encourage biocompatibility during use by a user. Preferably, the selective coating 170 comprises at least one complementary molecule 171 (e.g., ionophore, protein, peptide, amino acid, etc.) to a target analyte/ion distributed within a polymer matrix 172, as shown in FIG. 2A. Preferably, the complementary molecule 171 is evenly dispersed throughout the polymer matrix 172; however, the complementary molecule 171 can alternatively be localized within regions of the polymer matrix 172 in a heterogeneous manner. In examples, the complementary molecule is valinomycin/potassium tetrakis for potassium sensing, 4-tert-Butylcalix[4]arene-tetraacetic acid tetraethyl ester for sodium sensing, (–)-(R,R)—N,N'-Bis-[11-(ethoxycarbonyl) undecyl]-N,N',4,5-tetramethyl-3,6-dioxaoctane-diamide, Diethyl N,N'-[(4R,5R)-4,5-dimethyl-1,8-dioxo-3,6-dioxaoctamethylene] bis (12-methylaminododecanoate) for calcium sensing, and meso-Tetraphenylporphyrin manganese(III)-chloride complex for chloride sensing, according to ion-selective reactions. In an example, the polymer matrix 172 is composed of polyvinyl chloride (PVC) with a plasticizer to affect flexibility of the polymer matrix; however, the polymer matrix 172 can additionally or alternatively be composed of any other suitable polymer (e.g., polyethylene, polytetrafluoroethylene, urethane, parylene, nafion, polyvinyl chloride, polyvinyl alcohol, polyvinyl butyral, polydimethylsiloxane, fluorinated polymers, cellulose acetate, etc.) or non-polymer (e.g., oxide, nitride, carbide, etc.) configured to contain a distribution of complementary molecules. Additionally, the selective coating 170 may not comprise a plasticizer. The selective coating 170 is preferably defined by a thickness that characterizes a rate at which complementary molecules bind to target analytes (e.g., diffusion rate), and that also characterizes the amount (e.g., concentration or total amount) of complementary molecules within the selective coating 170. Additionally, the polymer matrix 172 can contain additives and can additionally or alternatively be processed (e.g., with polar functional groups) to improve its adhesion to the filament 120 and to prevent delamination as the filament 120 is inserted into a user's skin. In examples, additives of the polymer matrix 172 can include amino-silicanes, polyhydroxy-ether imides, butylated silica, and heterogeneous oxidizers.

In other variations, the selective coating 170 of the filament 120 can additionally or alternatively function to enable amperometric detection of molecules (e.g., glucose, creatinine) using immobilized enzymes. In these variations, the selective coating 170 can be replaced by or may further comprise a layer of immobilized enzyme (e.g., glucose oxidase for glucose, creatine amidinohydrolase for creatinine) that functions to catalyze a reaction of the analyte to produce a mediator species (e.g., hydrogen peroxide), wherein the concentration of the mediatior species can be amperometrically detected via oxidation or reduction at a surface of the conductive layer 140 or the sensing layer 160. In one example, glucose is oxidized by glucose oxidase to generate hydrogen peroxide. The generated hydrogen peroxide is then hydrolyzed by a conducting surface (e.g., a platinum conducting layer) while it is held at an electric potential. In a variation of this example, the conducting surface may alternatively not be held at an electric potential, for instance, in cases wherein molecular or other species (e.g., iron hexacyanoferrate) serve as a layer of transduction. Furthermore, in other variations of this example, other oxidases (e.g. alcohol oxidase, D- and L-amino acid oxidases, cholesterol oxidase, galactose oxidase, urate oxidase, etc.) can be used in a similar manner for the analysis of their complements.

In variations of the sensing layer including a layer of immobilized enzymes, the layer of immobilized enzymes can be covered by one or more membranes, which functions to control the diffusion rate and/or concentrations of analyte, mediator species (e.g., hydrogen peroxide, ferrocene), or interfering species (e.g., uric acid, lactic acid, ascorbic acid, acetaminophen, oxygen). The membrane(s) can also function to provide mechanical stability. In examples, the membrane(s) can include any one or more of: polyurethanes, nafion, cellulose acetate, polyvinyl alcohol, polyvinyl chloride, polydimethylsiloxane, parylene, polyvinyl butyrate and any other suitable membrane material.

As shown in FIG. 2E, any filament 120 of the array of filaments 110 can further comprise an adhesion coating 180, which functions to maintain contact between layers, coatings, and/or substrates of the filament 120. The adhesion coating 180 can further function to bond the layers, coatings, and/or substrates, and can prevent delamination between the layers, coatings, and/or substrates. The adhesion coating 180 is preferably an appropriately bio-safe, anti-inflammatory, and anti-microbial material, and preferably maintains contact between layers, coatings, and/or substrates of the filament 120 over the lifetime usage of the microsensor 100. In examples, the adhesion coating 180 is composed of any one or more of: a polyurethane, nafion, cellulose acetate, polyvinyl alcohol, polyvinyl butyrate, polyvinyl chloride, polydimethylsiloxane, paralyene, any material used in variations of the selective coating 170, and any other suitable adhesion material. However, in variations, a filament 120 of the microsensor 100 can alternatively not comprise an adhesion coating 180. Alternatively, layers, coatings, and/or substrates of the filament can be treated (e.g., heat treated, ultraviolet radiation treated, chemically bonded, etc.) and/or processed such that appropriate contact is maintained, even without an adhesion coating 180.

As shown in FIG. 2F, any filament 120 can further comprise a temporary functional layer 190, which functions to facilitate penetration of a filament 120 into the body. After the filament 120 has penetrated the body, the temporary functional layer 190 is preferably configured to dissolve or be absorbed by the body, leaving other portions of the filament 120 to operate to detect target analytes/ions characterizing a user's body chemistry. The temporary functional layer 190 can be configured, such that the sensing layer 160 is at an appropriate depth for detection (e.g., has access to interstitial fluid below the user's stratum corneum), once the temporary functional layer 190 has penetrated the user's body. The temporary functional layer 190 is preferably composed of an inert, bioabsorbable material that is porous; however, the temporary functional layer 190 can alternatively not be porous or bioabsorbable. In some variations, the temporary functional layer 190 can be configured to release an initial ion concentration with a known release profile (e.g., spiked or continuous release) in order to calibrate the microsensor 100. In specific examples, the temporary functional layer 190 can include a nitride material (e.g., 1000-2500 Å thick nitride), an oxide material, a carbide material, a salt, a sugar, a polymer (e.g., polyethylene glycol), and/or any other suitable material that does not deteriorate during subsequent processing steps. Other variations of the filament can further comprise any other suitable temporary functional layer 190 providing any other suitable function.

Any filament 120 of the microsensor 100 can further comprise any other appropriate functional layer or coating. In variations, a filament 120 can comprise layers or coatings that perform any one or more of the following functions: suppress or prevent an inflammatory response (e.g., by comprising a surface treatment or an anti-inflammatory agent), prevent bio-rejection, prevent encapsulation (e.g., by comprising a bio-inert substance, such as pyrolytic carbon), enhance target analyte/ion detection, and provide any other suitable anti-failure mechanism for the array of filaments 110. In one such variation, a filament 120 of the microsensor 100 can include a biocompatible layer 185 appropriately situated (e.g., situated deeper than a temporary functional layer 190, situated superficial to an adhesion layer, etc.) to enhance biocompatibility of the filament 120. In examples, the biocompatible layer 185 can include a polymer (e.g., urethane, parylene, teflon, fluorinated polymer, etc.) or any other suitable biocompatible material. In another variation, a filament 120 of the microsensor 100 can additionally or alternatively include an intermediate protective layer 166 appropriately situated (e.g., situated deeper than a selective layer 170, etc.), which functions as an optional layer to provide intermediate protection and/or block transport of undesired species. In examples, the intermediate protective layer can include a polymer (e.g., teflon, chlorinated polymer, nafion, polyethylene glycol, etc.) and can include functional compounds (e.g., lipids, charged chemical species that block transport of charged species, etc.) configured to provide a protective barrier. In another variation, a filament 120 of the microsensor 100 can additionally or alternatively include a stabilizing layer 163 appropriately situated (e.g., situated deeper than an intermediate protective layer 166, situated deeper than a selective layer 170, situated superficial to a sensing layer 160, etc.), which functions to stabilize the sensing layer 160. In one example, the stabilizing layer 163 can include a polymer (e.g., electropolymerized phenylenediamine) acting to stabilize a glucose-oxidase sensing layer 160. In another variation, a filament 120 of the microsensor 100 can additionally or alternatively include an intermediate selective layer 145 appropriately situated (e.g., situated deeper than a sensing layer 160, situated superficial to a conductive layer 140, etc.), which functions to provide an additional selective layer. The intermediate selective layer can include or be coupled to an immobilized complementary molecule (e.g., glucose oxidase) to facilitate analyte detection. In an example, the intermediate selective layer 145 includes a polymer (e.g., electropolymerized phenylenediamine) and is situated superficial to a conductive layer 140; however, in variations of the example, the intermediate selective layer 145 can include any other suitable selective material and can be situated relative to other layers in any other suitable manner. In another variation, a filament 120 of the microsensor 100 can additionally or alternatively include an intermediate active layer 143 appropriately situated (e.g., situated deeper than an intermediate selective layer 145, situated deeper than a sensing layer 143, situated superficial to a conductive layer 140, etc.), which functions to facilitate transduction of a signal. As such, the intermediate active layer 143 can facilitate transduction in variations wherein the conductive layer 140 is not held at a given potential, and/or can facilitate transduction in any other suitable manner. In one example, the intermediate active layer 143 comprises iron hexacyanoferrate (i.e., Prussian Blue) and in another example, the intermediate active layer 143 comprises nano-Platinum; however, the intermediate active layer 143 can additionally or alternatively include any other suitable material.

In any of the above embodiments, variations, and examples, any one or more of layers 185, 166, 163, 145, 143 can isolated to a desired region of the filament 120, or can non-discriminately coat an entire surface of the filament 120 at a given depth. Furthermore, any filament 120 of the microsensor 100 can include multiple instances of any layer or coating 140, 143, 145, 150, 160, 163, 166, 170, 180, 185 190, can omit a layer or coating 140, 143, 145, 150, 160, 163, 166, 170, 180, 185 190, and/or can include layers or coatings arranged in any other suitable manner different from the variations and examples described above and below. In one such variation, a different configuration of layers can allow selective passage of molecules having different properties (e.g., chemistries, size). However, any suitable configuration of a filament 120 can be provided for any other suitable application.

As shown in FIG. 3, each filament 120 of the array of filaments 110 can have one of a variation of geometries. In a first geometric variation a filament 120 can be solid, examples of which are shown in FIGS. 3B and 3D-3G. In a first example of the solid filament 120, the solid filament 120 can have a profile tapering continuously to at least one point (e.g., pyramid or conical shaped with one or more pointed tips), and can have straight or curved edges, as shown in FIGS. 3B, 3D, and 3G. In variations, the point(s) of the filament 120 can be defined by any suitable number of faces. In a second example of the solid filament 120, the solid filament 120 can comprise two regions—a pointed tip region 121 configured to pierce a user's skin, and a blunt region 122 (e.g., a columnar protrusion, a pillar), coupled to the pointed tip region, as shown in FIG. 3E. The pointed tip region 121 can be configured to be bioabsorbable, dissolve (e.g., using a degradable material) or, in an extreme example, break off (e.g., using an engineered stress concentration) and be expelled from a user's system after the solid filament 120 has penetrated the user's skin; however, the pointed tip region 121 can alternatively be configured to remain attached to the solid filament 120 after the solid filament 120 has penetrated the user's skin. In a third example of the solid filament 120, the solid filament 120 can comprise two regions—a barbed tip region 123 including a barb configured to penetrate a user's skin and promote skin adherence, and a second region 122 coupled to the barbed tip region, as shown in FIG. 3F. In the third example of the solid filament 120, the barbed tip region can be configured to have one sharp protrusion for skin penetration, or can alternatively be configured to have multiple sharp protrusions for skin penetration.

Figure 3A:
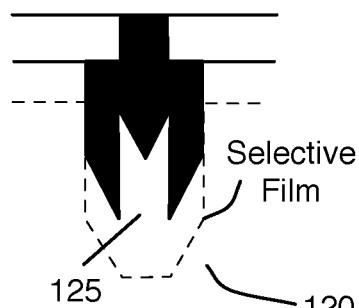
FIGS. 3A-3H depict embodiments of filament geometries.
Figure 3B:
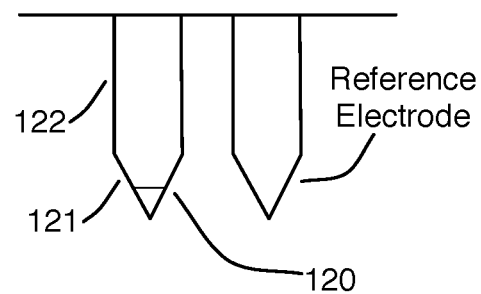
Figure 3C:
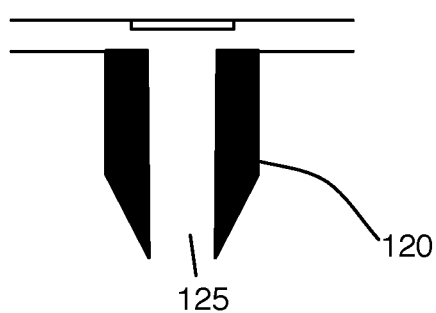
Figure 3D:
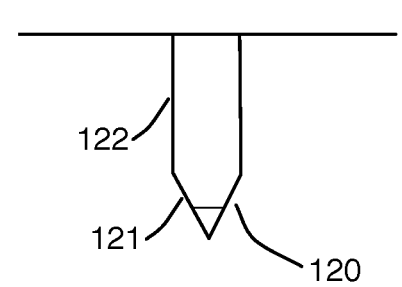
Figure 3E:
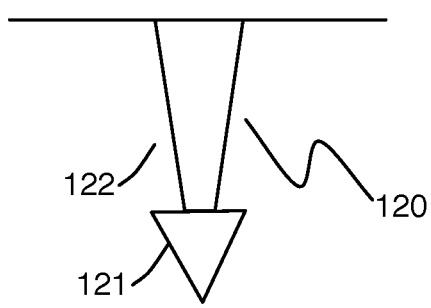
Figure 3F:
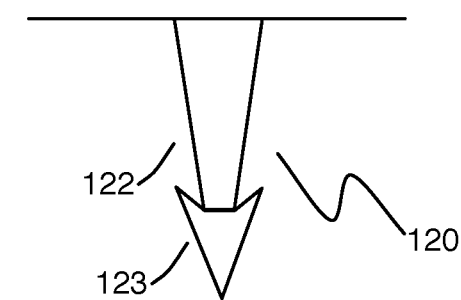
Figure 3G:
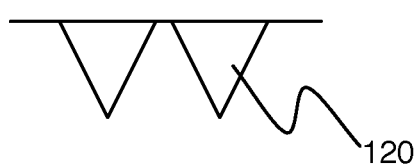
Figure 3H:
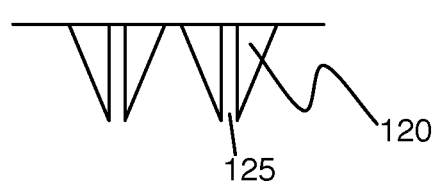

In a second geometric variation, examples of which are shown in FIGS. 3A, 3C, and 3H, a filament 120 can be hollow and comprise a channel 125 within an interior region of the hollow filament 120. In a first example of the hollow filament 120, the hollow filament 120 can have a profile tapering continuously to at least one point (e.g., pyramid or conical shaped with one or more pointed tips), and can have straight or curved edges. Furthermore, the point(s) of the filament 120 can be defined by any suitable number of faces. In the first example of the hollow filament 120, the hollow filament 120 can additionally be processed to have one or more channels 125 configured to facilitate sensing of an analyte characterize a user's body chemistry. In the first example, a channel 125 of the hollow filament 120 can be characterized by a uniform cross section along the length of the channel 125, or can alternatively be characterized by a non-uniform cross section along the length of the channel 125. In a second example of a hollow filament 120, the hollow filament 120 can be configured to receive a volume of the user's body fluid into a sensing chamber to facilitate analyte detection. In the second geometric variation, the hollow filament 120 can be composed of a metal or a semiconductor, or any appropriate material to facilitate analyte sensing. In other examples, the hollow filament 120 may implement a variation of any of the solid filaments described above, but be processed to have at least one channel 125 within an interior region of the hollow filament 120. Each filament 120 in the array of filaments 110 can include a combination of any of the above geometric variations, a different variation of the above geometric variations, and furthermore, the array of filaments 110 can comprise filaments characterized by different geometric variations.

Figure 5A:
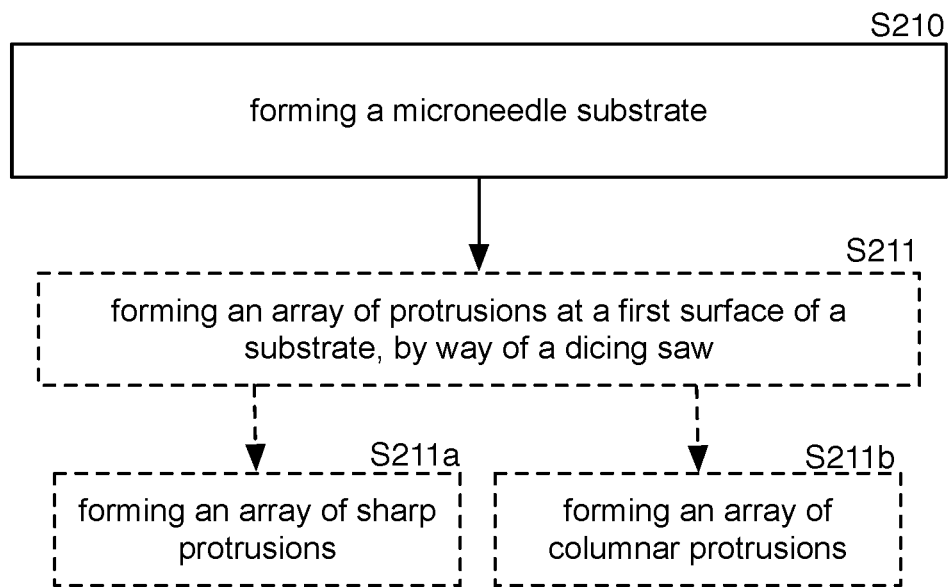
FIGS. 5A-5C depict embodiments of a portion of a manufacturing method for an on-body microsensor for biomonitoring.
Figure 5B:
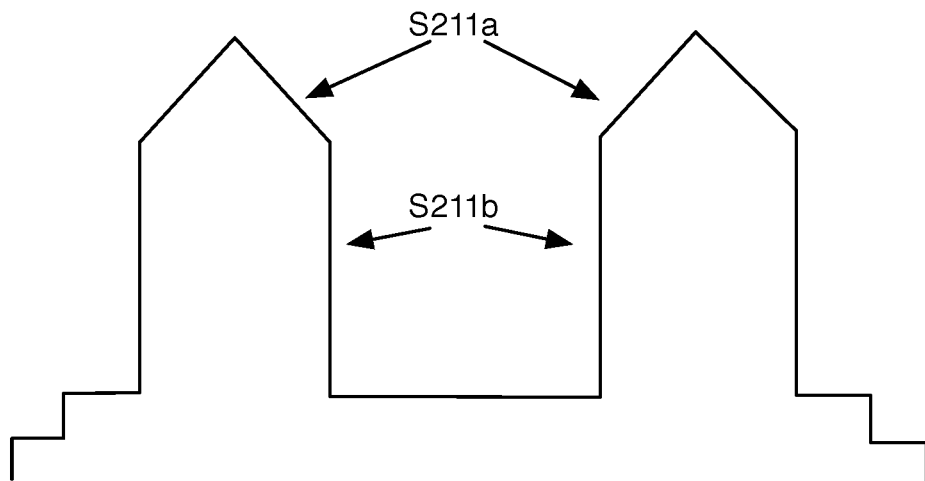
Figure 5C:
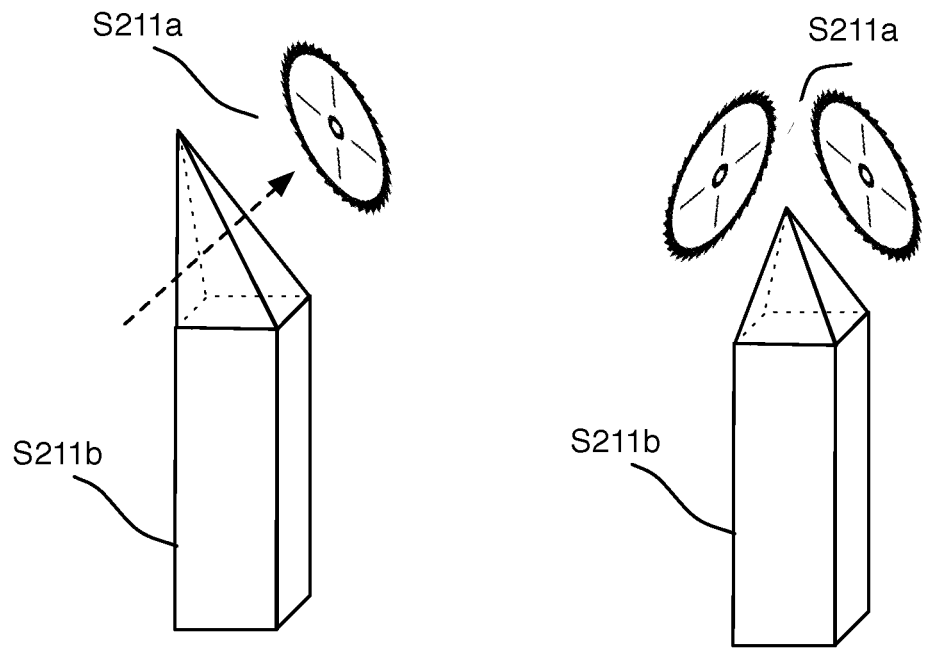
Figure 5C:
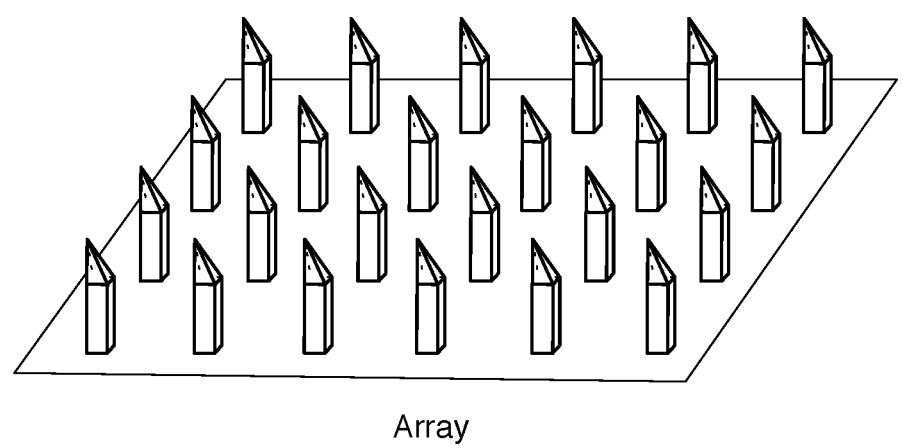

In a first specific example of a filament 120, as shown in FIG. 2A, a solid filament 120 comprises a uniform silicon substrate 130 composed to P-type, boron-doped orientation <100> silicon with a resistivity from 0.005-0.01 ohm-cm, a thickness of 500-1500 μm, and a TIV less than 10 μm, processed to define a substrate core with a pointed tip region 121 formed by way of a dicing saw, as described in Section 2 below. In the first specific example, the filament comprises a conductive layer 140 of nickel, coupled to the substrate 130 by electroplating, wherein the conductive layer 140 is isolated to the pointed tip region 121 of the substrate core, and to a face of the substrate 130 directly opposing the face including the filament 120. In the first specific example, the filament 120 further includes an insulating layer 150 of 1 μm oxide, formed by thermal growth at 900-1050 C for 1-2 hours, as described in further detail below, wherein the insulating layer 150 is formed at all exposed surfaces of the substrate 130 and defines an active region at the pointed tip region 121 of the filament 120. In variations of the first specific example, the conductive layer 140 can additionally or alternatively include one or more of a gold-based material and a platinum-based material. Furthermore, in the first specific example, the filament 120 can include a conductive polymer (polypyrrole) coating as the sensing layer 160 coupled to the conductive layer 140 at the pointed tip region 121 of the filament 120, and a PVC selective coating 170 with complementary molecules 171 to target analytes coupled to the sensing layer 160. In the first specific example, the solid filament 120 is includes a rectangular prismatic columnar protrusion, with a pointed tip region defined by four faces tapering to a point, as shown in FIG. 5C, wherein two of the four faces are orthogonal to each other and contiguous with two faces of the rectangular prismatic columnar protrusion, and wherein the other two faces are formed by way of a dicing saw with an angled blade, as described further in Section 2 below.

In a second specific example of a filament 120 for glucose sensing, which can be characterized as shown in FIG. 2B, a solid filament 120 comprises a uniform silicon substrate 130 composed to P-type, boron-doped orientation <100> silicon with a resistivity from 0.005-0.01 ohm-cm, a thickness of 500-1500 µm, and a TIN less than 10 µm, processed to define a substrate core with a pointed tip region 121 formed by way of a dicing saw, as described in Section 2 below. In the second specific example, the filament comprises a conductive layer 140 of nickel, gold, and platinum, coupled to the substrate 130 by electroplating, wherein the conductive layer 140 is isolated to the pointed tip region 121 of the substrate core, and to a face of the substrate 130 directly opposing the face including the filament 120. In the second specific example, the filament 120 further includes an insulating layer 150 of 0.1-10 µm oxide, formed by thermal growth at 900-1050 C for 1-2 hours, as described in further detail below, wherein the insulating layer 150 is formed at all exposed surfaces of the substrate 130 and defines an active region including the conductive layer 140 at the pointed tip region 121 of the filament 120. Furthermore, in the second specific example, the filament includes electropolymerized phenylenediamene, tyramine, glucose oxidase, and poly-lysine as the sensing layer 160 superficial to the conductive layer 140 at the pointed tip region 121 of the filament 120. In between the conductive layer 140 and the sensing layer 160 at the pointed tip region 121, the second specific example includes an intermediate selective layer 145 of electropolymerized phenylenediamine polymer coupled to an intermediate active layer 143 including iron hexacyanoferrate, coupled directly to the conductive layer 140. Finally the second specific example includes an intermediate protective layer 166 of urethane, coupled to a stabilizing layer 163 of phenylenediamine coupled to the sensing layer 160, surrounded by a PVC selective coating 170 with complementary molecules 171 to target analytes coupled to the sensing layer 160. In the second specific example, the solid filament 120 is includes a rectangular prismatic columnar protrusion, with a pointed tip region defined by four faces tapering to a point, as shown in FIG. 5C, wherein two of the four faces are orthogonal to each other and contiguous with two faces of the rectangular prismatic columnar protrusion, and wherein the other two faces are formed by way of a dicing saw with an angled blade, as described further in Section 2 below.

Figure 2C:
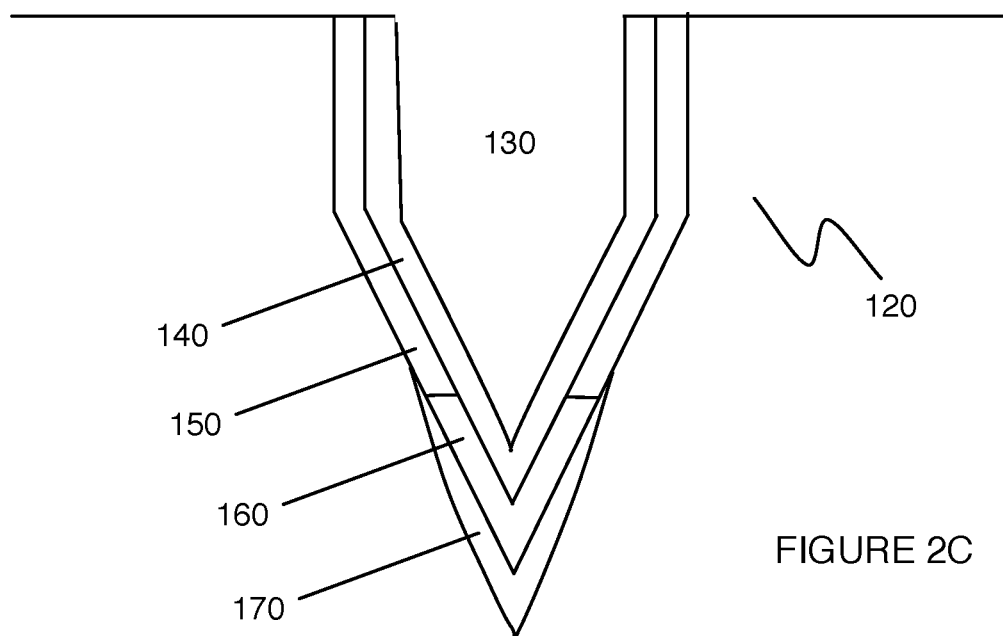
FIGS. 2C and 2D depict examples of filaments for biomonitoring.

In a third specific example of a filament 120, as shown in FIG. 2C, a solid filament 120 comprises a uniform silicon substrate 130, a conductive layer 140 of platinum at the tip of the filament 120, an insulating layer 150 composed of polyimide isolating the active region of the filament 120 to the tip of the filament, a conductive polymer (polypyrrole) coating as the sensing layer 160, and a PVC selective coating 170 with complementary molecules 171 to target analytes. In the third specific example, the solid filament 120 is conical and has a profile tapering to a single sharp point.

Figure 2D:
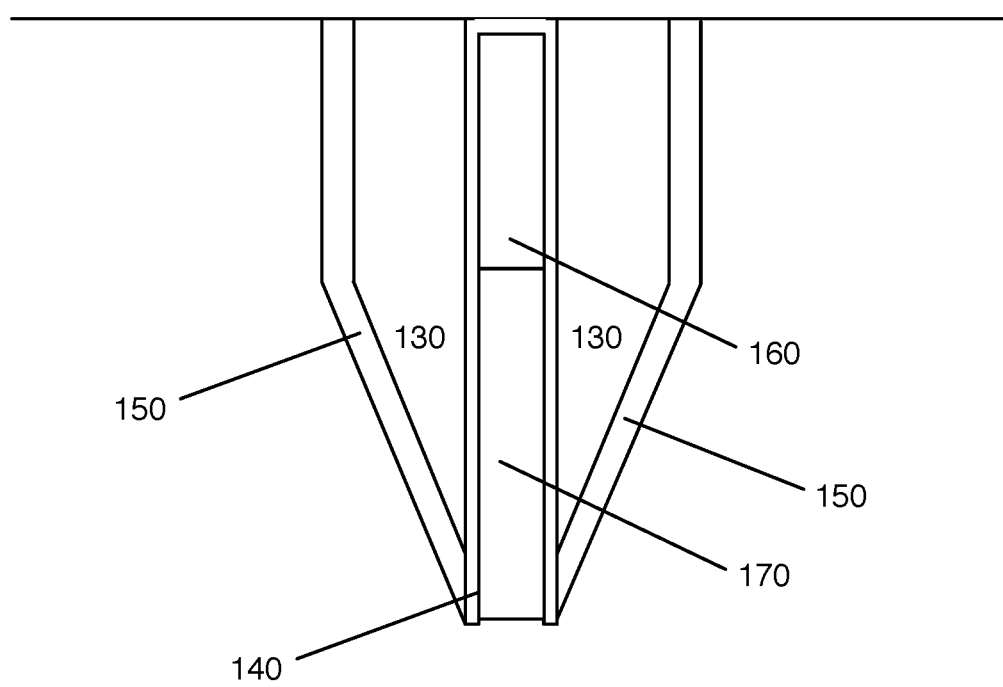
Figure 2E:
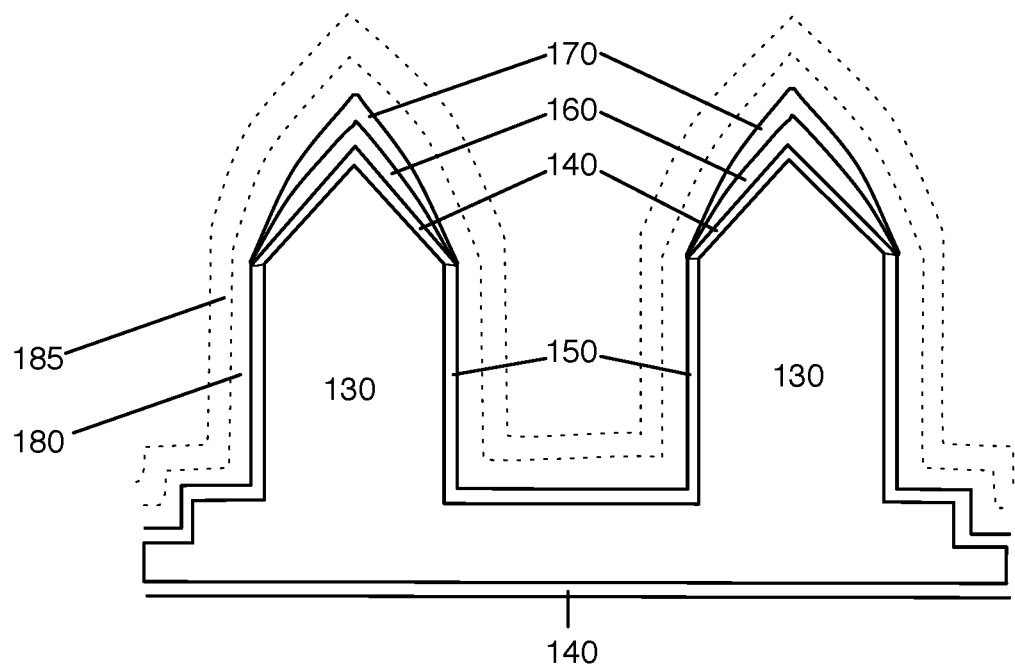
FIG. 2E depicts an example of a filament, comprising an adhesion layer, for biomonitoring.
Figure 2F:
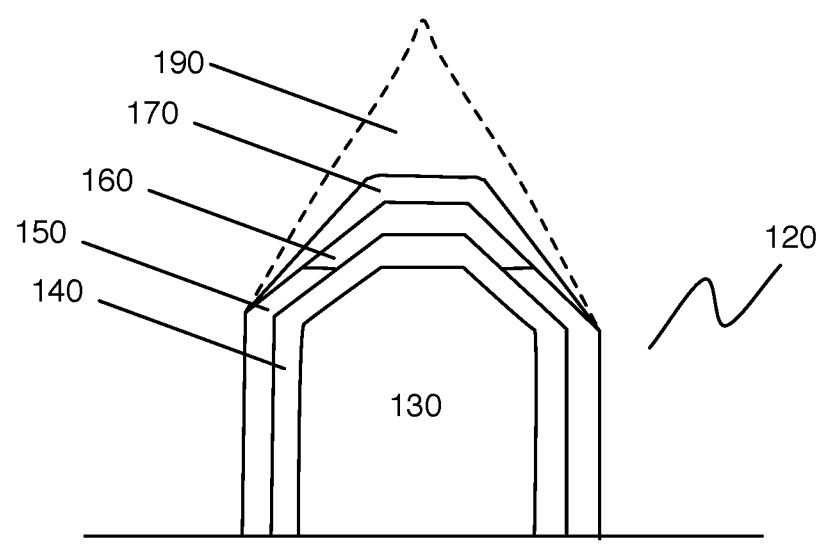
FIG. 2F depicts an example of a filament, comprising a temporary functional layer, for biomonitoring.

In a fourth specific example of a filament 120, as shown in FIG. 2D, a hollow filament 120 comprises a uniform silicon substrate 130, an external surface coated with an insulating layer 150 composed of polyimide, a conductive layer 140 of platinum covering the surface of an interior channel 125, a conductive polymer (polypyrrole) coating as a sensing layer 160 covering the conductive layer 140 of platinum, and a selective PVC coating 170 covering the sensing layer 160. In the fourth specific example, the hollow filament 120 is conical with a single cylindrical channel 125 passing through the axis of rotation of the conical filament 120.

Each filament 120 in the array of filaments 110 can also be structured as any appropriate combination of the above variations and/or examples of filament 120 composition and/or geometry, and/or can be paired with a filament 120 serving as a reference electrode configured to normalize a signal detected in response to analyte sensing. Additionally, the array of filaments 110 can comprise filaments characterized by different variations of filament composition (e.g., composition of layers and/or coatings).

2. Manufacturing Method

Figure 4:
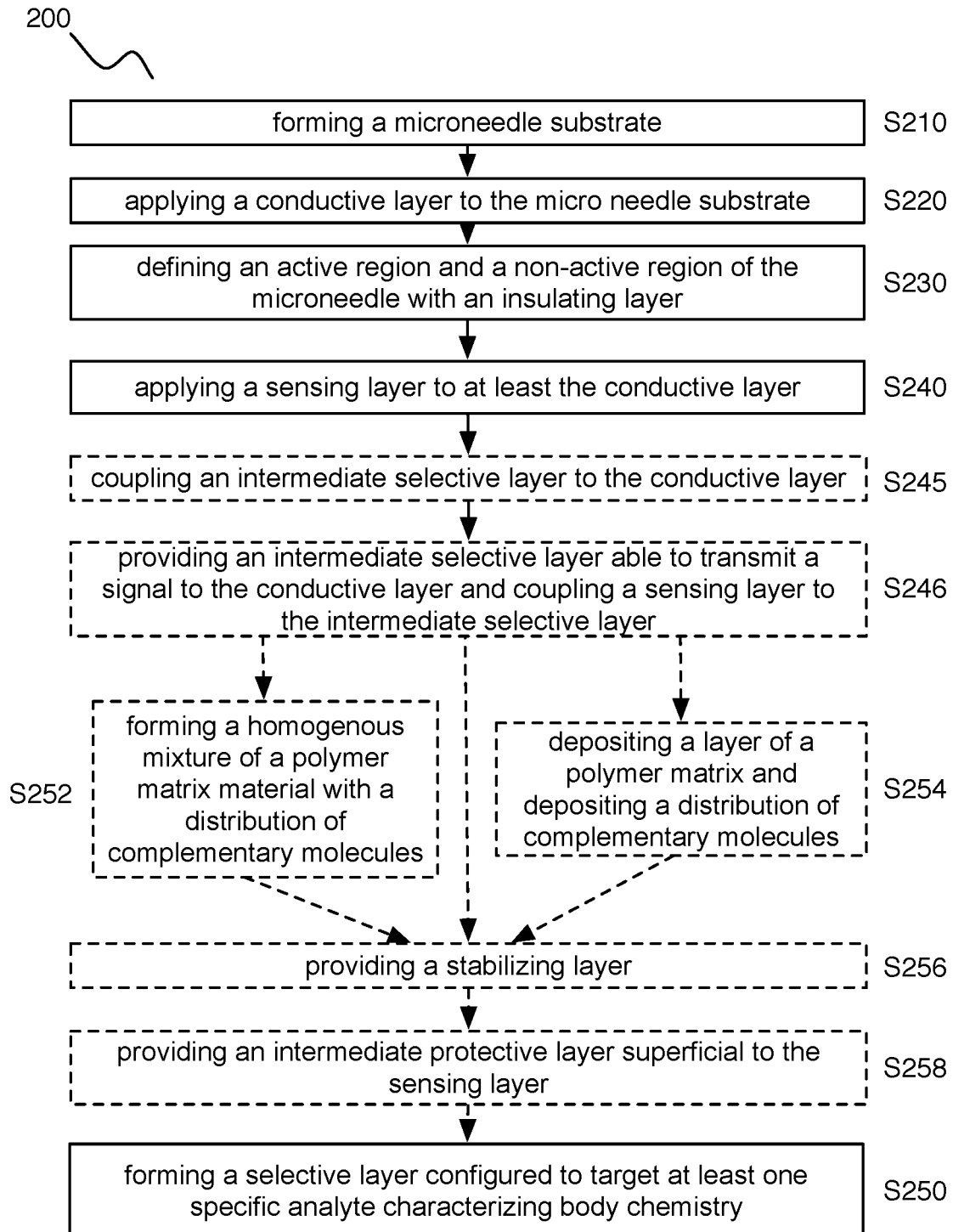
FIG. 4 depicts an embodiment of a manufacturing method for an on-body microsensor for biomonitoring.

As shown in FIG. 4, an embodiment of a manufacturing method 200 for the microsensor comprises forming a filament substrate S210; applying a conductive layer to the filament substrate S220; defining an active region and a non-active region of the filament with an insulating layer S230; applying a sensing layer to at least the conductive layer S240; and forming a selective layer S250, coupled to the sensing layer, configured to target at least one specific analyte characterizing body chemistry. The manufacturing method 200 functions to form an array of filaments as part of a microsensor for monitoring body chemistry. Preferably, the manufacturing method 200 forms an array of substantially identical filaments, wherein each filament in the array of filaments comprises an active region for analyte detection, and a non-active region comprising an insulating layer. Alternatively, the manufacturing method 200 can form an array of substantially non-identical filaments, with different portions of the array having different functionalities and/or configurations.

2.1 Manufacturing Method—Substrate, Conductive Layer, and Insulating Layer Processing Block S210 recites forming a filament substrate, and functions to form a core or base structure upon which other layers or coatings can be applied, in order to facilitate processing of each filament for specific functionalities. As shown in FIG. 5A, in a first variation, Block S210 includes forming an array of protrusions at a first surface of the substrate, by way of a dicing saw S211. In variations of Block S211, forming an array of protrusions can include forming an array of sharp protrusions S211a, as shown in FIGS. 5B and 5C, by way of an angled blade (e.g., a 60 degree blade, a 45 degree blade) of a dicing saw or other saw characterized by a desired depth (e.g., 150-500 µm), configured to cut a desired number of facet-filament tips (e.g., 2-facet tips, 4-facet tips, 6-facet tips, etc.) at a desired rate (e.g., 1-10 mm/s). In block S211a, the dicing saw can be configured to form the array of sharp protrusions through adjacent cuts in a first direction, followed by adjacent cuts in a second direction (e.g., orthogonal to the first direction), thereby forming a 2-dimensional array of sharp protrusions (i.e., sharp tips). However, any suitable number of cuts in any suitable number of directions can be used to form the array. Additionally or alternatively, forming the array of protrusions in Block S211 can including forming an array of columnar protrusions S211b at the first surface of the substrate, by way of a non-angled blade of a dicing saw of a desired depth (e.g., 25-500 µm) and width (e.g., 75-200 µm) with a desired gap (e.g., 25-2000 µm), configured to cut a desired number of columnar protrusions at a desired rate (e.g., 1-10 mm/s), wherein each columnar protrusion defines any suitable cross sectional profile (e.g., polygonal, non-polygonal). In block S211b, the dicing saw can be configured to form the array of columnar protrusions through adjacent cuts in a first direction, followed by adjacent cuts in a second direction (e.g., orthogonal to the first direction), thereby forming a 2-dimensional array of columnar protrusions. However, any suitable number of cuts in any suitable number of directions can be used to form the array.

In variations of Block S211, Blocks S211a and S211b preferably form protrusions with a sharp tip defined at the end of each columnar protrusion in a one-to-one manner, as shown in FIG. 5B, wherein the sharp tip is substantially aligned with and contiguous with a respective columnar protrusion: however, the sharp tip(s) can be non-aligned with a respective columnar protrusion, can be non-contiguous with a respective columnar protrusion, and/or can be formed in a non-one-to-one manner with the array of columnar protrusions. In some variations, a sharp tip can comprise a pyramidal tip region defined by an irregular pyramid, having a first pair of orthogonal faces, substantially contiguous with two faces of the columnar protrusion, and a second pair of orthogonal faces, angled relative to the first pair of orthogonal faces, such that the tip is substantially aligned with a vertex of the rectangular cross section of the columnar protrusion; however, in other variations, the tip can be misaligned with a vertex of the rectangular cross section of the columnar protrusion. Furthermore, Blocks S211a and S211b can be performed in any suitable order, in order to facilitate application of the conductive layer to the filament substrate in variations of Block S220 and/or defining an active region and a non-active region of the filament with an insulating layer, in variations of Block S230. In still further variations, alternatives to the first variation of Block S210 can include forming the array of protrusions at the first surface of the substrate by way of any other suitable method of bulk material removal.

In the first variation, the substrate can be composed of a semiconducting material (e.g., silicon, quartz, gallium arsenide), a conducting material (e.g., gold, steel, platinum), and/or an insulating material (e.g., glass, ceramic). In some variations, the substrate 130 can comprise a combination of materials (e.g., as in a composite, as in an alloy). In a specific example, the substrate is composed of P-type, boron-doped, <100> orientation silicon with a resistivity of 0.005-0.01 ohm-cm, a thickness from 500-1500 μm, and a TIN of <10 μm, with a first surface side polish. In variations of the specific example, the substrate 130 can be composed of silicon with any other suitable type, doping, miller index orientation, resistivity, thickness, TIV, and/or polish.

Figure 6A:
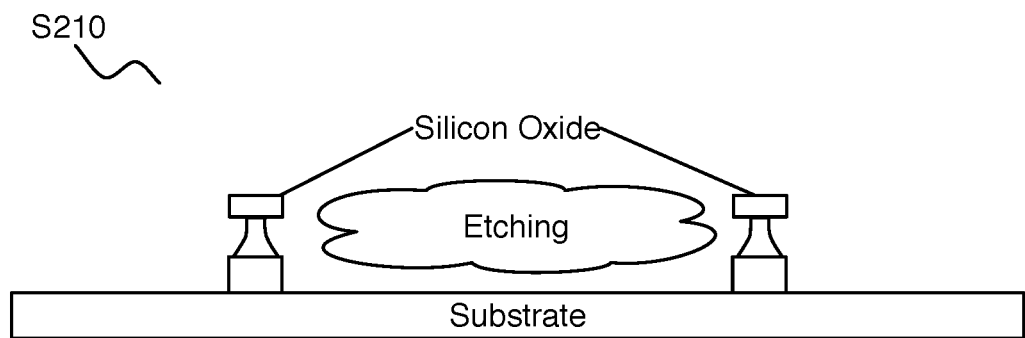
FIGS. 6A and 6B depict variations of forming a filament substrate.

As shown in FIG. 6A, in a second variation, Block S210 comprises creating a substrate, applying a photoresist to the substrate, and etching the substrate to form the filament substrate. The second variation of Block S210 preferably defines an array of sharp protrusions, wherein each sharp protrusion has a base end, coupled to the substrate, a sharp tip end, and a rotational axis of symmetry defined between the base end and the sharp tip end. In variations, each sharp protrusion can be defined by an inwardly tapering profile, such that sharp protrusion has a base end defined by a first width (or diameter), and widens from the base end for at least a portion of the length of the sharp protrusion. However, the second variation of Block S210 can include forming protrusions, defined by any other suitable profile, at the substrate. The second variation can comprise performing a Bosch process, a deep-reactive ion etching (DRIE) process, any suitable etch (e.g., a potassium hydroxide etch), or any other suitable process to form the filament substrate. In a specific example of the second variation, the substrate comprises a P++ and/or silicon-doped silicon wafer with an oxide pad, a negative photoresist is applied in a uniform pattern to the oxide pad, and potassium hydroxide anisotropic etching is used to form the filament substrate. In further detail regarding the specific example, the substrate is composed of P-type, boron-doped, <100> orientation silicon with a resistivity of 0.005-0.01 ohm-cm, a thickness from 500-1500 μm, and a TTV of <10 μm, with a first surface side polish. In variations of the specific example, the substrate 130 can be composed of silicon with any other suitable type, doping, miller index orientation, resistivity, thickness, TTV, and/or polish. In alternative examples of the second variation, Block S210 can comprise using any appropriate semiconductor substrate, applying a positive photoresist and/or a negative photoresist to the semiconductor substrate, applying the photoresist in a non-uniform pattern, and/or using any appropriate etching method (e.g., anisotropic, isotropic) to form the filament substrate.

Figure 6B:
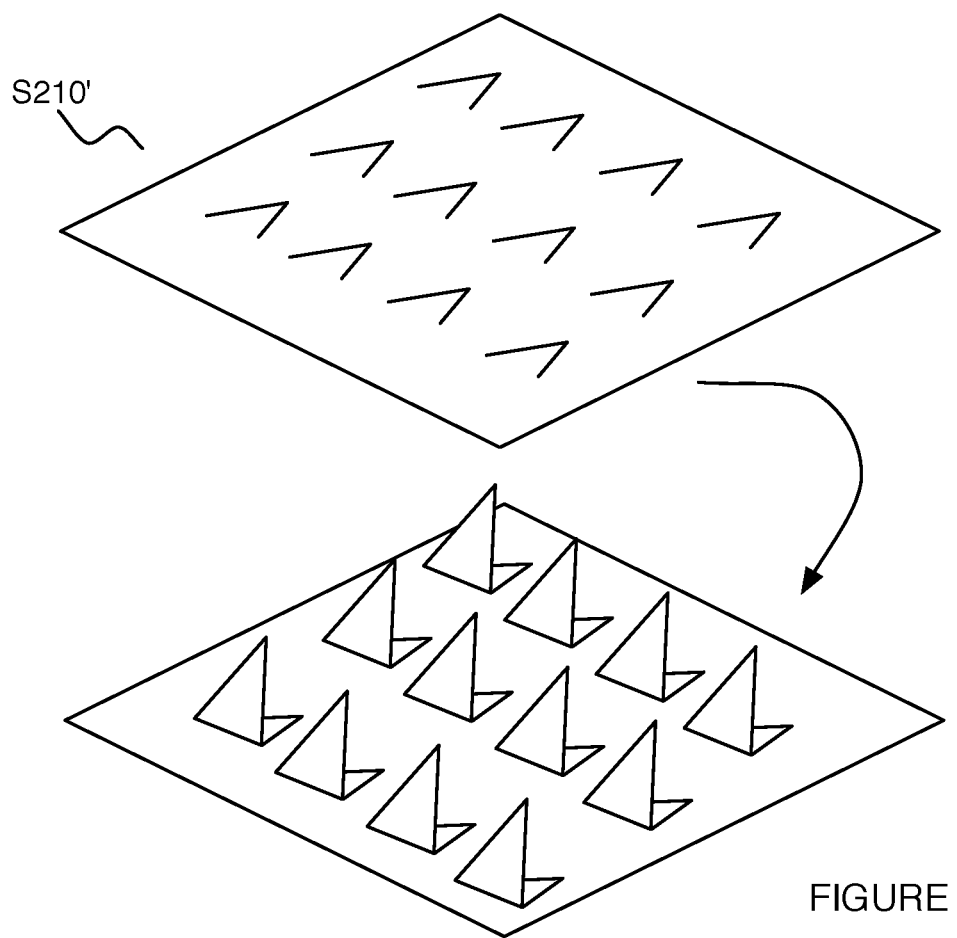

In a third variation, as shown in FIG. 6B, Block S210' comprises etching an array into a ductile substrate and deforming the array to form an array of protrusions, thus forming a filament substrate. In a specific example of the third variation, an array of v-shaped features is laser-etched into a ductile steel substrate, and each v-shaped feature in the array of v-shaped features is then deformed outward from the steel substrate by 90° to form an array of v-shaped filament protrusions. Alternative examples of the third variation can include etching the array using any appropriate method (e.g., punching, die-cutting, water cutting), etching any appropriate array feature (e.g., any pointed feature), and deforming the array in any appropriate manner (e.g., by any angular amount for each or all array features) to form the array of protrusions. In alternative variations, the filament substrate can be formed by any other suitable method (e.g., molding, laser cutting, stamping, 3D printing, etc.).

Block S220 recites applying a conductive layer to the filament substrate S220, and functions to form a conductive "active" region to facilitate signal transmission upon detection of an analyte by a filament of the microsensor. Preferably, Block S220 comprises coupling a conductive layer to the sharp tip of each columnar protrusion in the array of columnar protrusions formed, for example, in variations of Block S211a and S211b. In variations, coupling the conductive layer can include electroplating a conductive material or alloy of a conductive material (e.g., nickel, silver, iridium, tungsten, titanium, titanium nitride, aluminum, cadmium, chromium, molybdenum, lead, gold, platinum, etc.) to the sharp tip of each columnar protrusion. Block S220 can additionally or alternatively comprise metalizing the filament substrate by sputtering a layer of any appropriate conductive material (e.g., gold, platinum, doped silicon, nickel, silver, iridium, tungsten, titanium, titanium nitride, aluminum, cadmium, chromium, molybdenum, lead, etc.) onto the filament substrate. In still other variations, however, Block S220 can alternatively or additionally comprise metalizing the filament substrate by plating or evaporating a layer of any appropriate conductive material onto the filament substrate, or by applying the conductive material (e.g., nickel, gold, platinum, doped silicon, tungsten, iridium, titanium nitride) in any other suitable manner. In addition to applying the conductive material to the sharp tips of the array of protrusions defined in Block S210, Block S220 can include coupling a second conductive layer to a second surface of the substrate (e.g., a surface of the substrate directly opposing the array of protrusions), in order to define a second conductive surface of the substrate to facilitate electrical coupling for signal transmission (e.g., upon detection of an analyte).

Preferably, Block S220 comprises applying the conductive layer to the filament substrate in a substantially uniform manner (e.g., as an even layer with substantially uniform thickness); however, Block S220 can alternatively comprise applying the conductive layer to the filament substrate in a non-uniform manner, such that some regions of the conductive layer are thicker than others. Furthermore, Block S220 can include application of multiple layers of one or more conductive materials, in order to form a conductive layer comprising multiple layers of materials. In variations involving sputtering or evaporation, the filament substrate can be translated or rotated while being sputter coated or evaporation coated to facilitate uniform deposition of the conductive layer. In variations involving plating to apply the conductive layer, the plating can be applied using chemical or electrochemical plating, to any appropriate thickness.

Block S230 recites defining an active region and a non-active region of the filament with an insulating layer, and functions to form at least one insulating region of a filament of the microsensor. Preferably, Block S230 comprises applying an insulating layer to a portion of the filament substrate/conductive layer assembly, in a manner wherein at least one region of the conductive layer is not covered (e.g., uncovered, exposed, unsheathed) with the insulating layer (thus forming the active and non-active regions of the filament). Block S230 can be performed using thermal oxide growth, spin coating, spray coating, or any other appropriate method of depositing a localized layer of an insulting material. Preferably, the insulating layer is composed of an insulating oxide; however, the insulating layer can additionally or alternatively include an insulating polymer (e.g., polyimide, cyanate ester) that is chemical and heat resistant and/or any appropriate material (e.g., thermally grown silicon oxide, chemical vapor deposited oxides, titanium oxide, tantalum oxide, other oxides, chemical vapor deposited nitrides, other nitrides, paralene, etc.) that is configured to insulate a portion of the filament substrate/conductive layer assembly. Furthermore, in Block S230, the insulating layer can be grown or deposited uniformly or non-uniformly over desired surfaces (e.g., all exposed surfaces, active regions formed through bulk material removal, active regions defined by chemical etching, plasma etching, high energy etching, any other suitable type of etching, etc.).

In a first example of Block S230, an oxide layer can be formed at exposed surfaces of the substrate (e.g., all exposed surfaces of the substrate, of substrate cores of protrusions, cut surfaces, etc.), by a thermal oxide growth process. The oxide layer preferably couples to the exposed surfaces of the substrate in a manner that discourages unbonding or removal of the oxide material during subsequent Blocks of the method 200. In the first example, the oxide layer is formed by way of a thermal oxide growth process at 900-1050 C for 1-2 hours, in order to induce 0.1-10 μm thick thermal oxide growth. In variations of the first example, however, the oxide layer can be formed at the substrate or coupled to the substrate using a thermal process defined by any suitable temperature parameters, for any suitable duration of time, in order to define an oxide layer of any other suitable thickness.

Figure 7A:
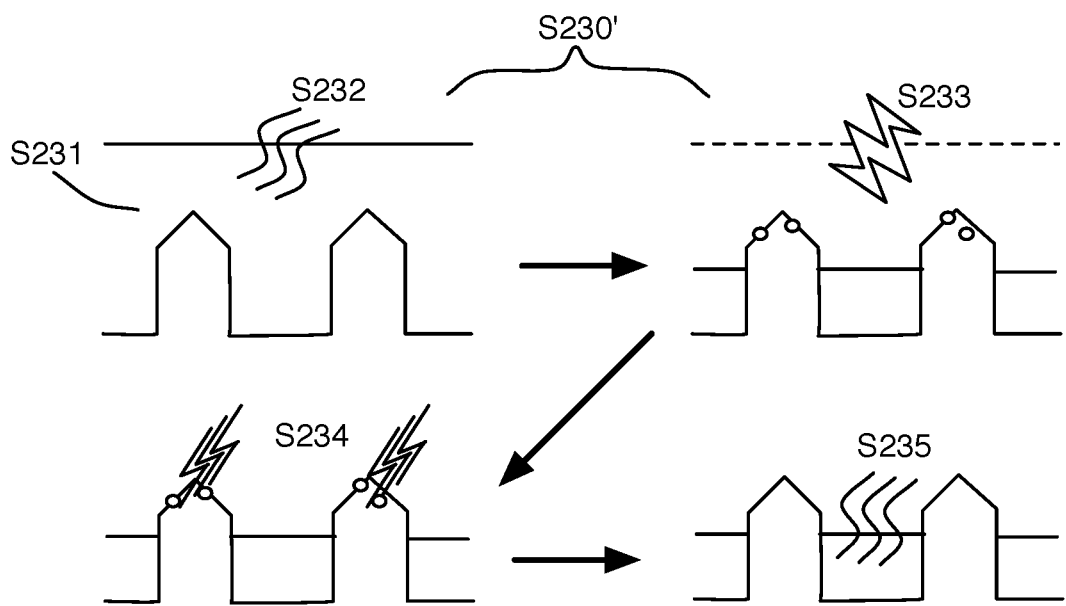
FIGS. 7A-7D depict variations of defining an active region and a non-active region of the filament with an insulating layer.

In a second example of Block S230', as shown in FIG. 7A, an insulating polymer (e.g., polyimide, cyanate ester) can be deposited over the substrate or substrate/conductive layer subassembly S231. The insulator may then be soft-baked S232 to facilitate selective removal of the insulating polymer. In the second example, the tip regions of the filaments can then be exposed by selectively dissolving or etching the soft-baked insulating polymer S233, and the tip regions of the filaments can be cleaned S234 (e.g., using a plasma-etching process). Finally, the filament assembly comprising active and non-active regions can be hard-baked to cure the insulating polymer S235. In a variation of the second example, the insulating polymer can be photosensitive, such that Block S232 uses a photolithographic process to selectively expose areas above filaments or between filaments (to increase solubility), and so that the a positive photolithographic process or a negative photolithographic process can be used to define the active/non-active regions. Additionally, Block S235 can use a photo-crosslinking process to cure the insulating polymer.

Figure 7B:
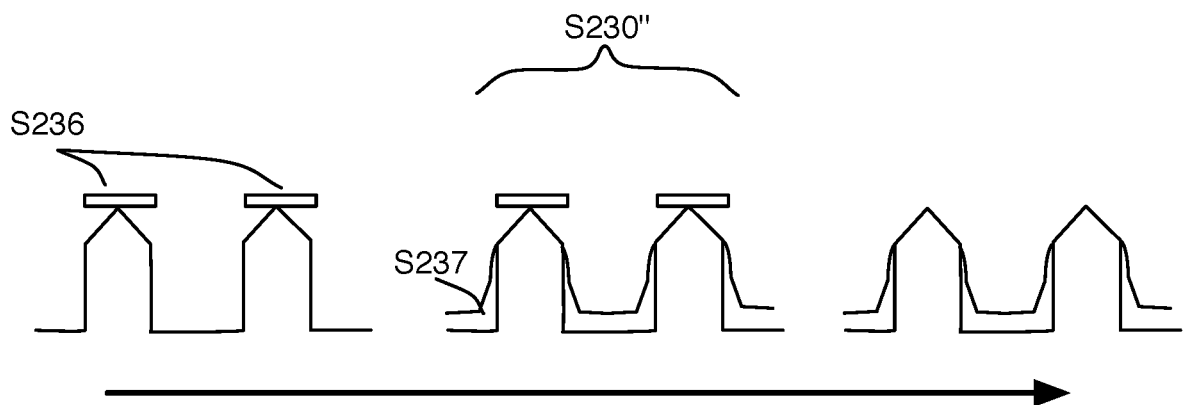

In a third example of Block S230", as shown in FIG. 7B, a set of oxide caps coupled to filament tips (produced, for instance, during a Bosch or DRIE process) can be used to shield the filament tips S236, and a dielectric or other insulating material can be applied to define active and non-active regions S237. The insulating material in the third example can be applied using a line of sight deposition method, preferably at an angle, such that the insulating material is applied only to specific regions (e.g., between filament tips). The line of sight deposition method can be an evaporation method (e.g., to deposit an insulating polymer), or can additionally or alternatively be a sputtering method (e.g., sputtering of titanium or tantalum), followed by oxidation to produce the insulating layer. The filament assembly can then be passivated (e.g., during a DRIE process) and the oxide caps can be removed (e.g., pinched off) to expose the active regions.

Figure 7C:
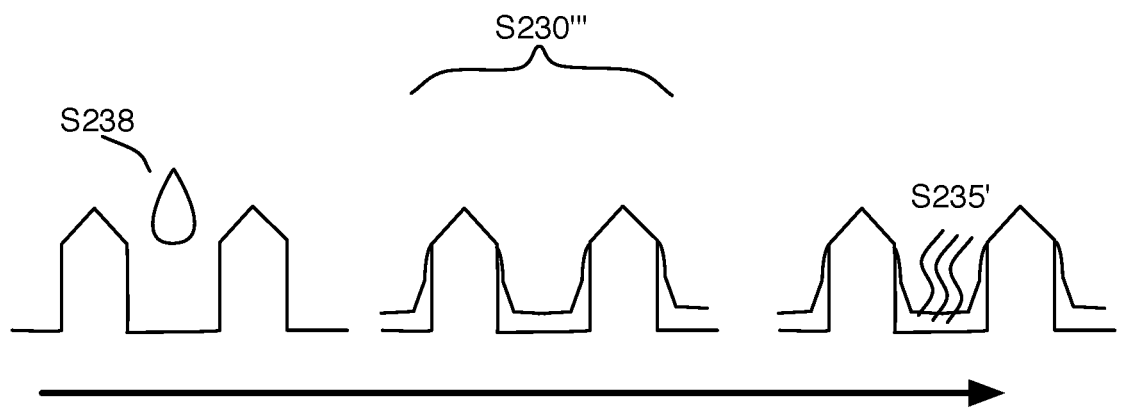

In a fourth example of Block S230''', as shown in FIG. 7C, the insulating material can be fluidly deposited between filament structures (e.g., by inkjet printing, silk screening, dispensing) S238. The insulating material can be a molten polymer (e.g., nylon), or can be a polymer that is in solution form (e.g., silicon, polyurethane, polyimide) that is subsequently cured S235' (e.g., baking, photo-crosslinking) to remove solvent and form the active and non-active regions.

Figure 7D:
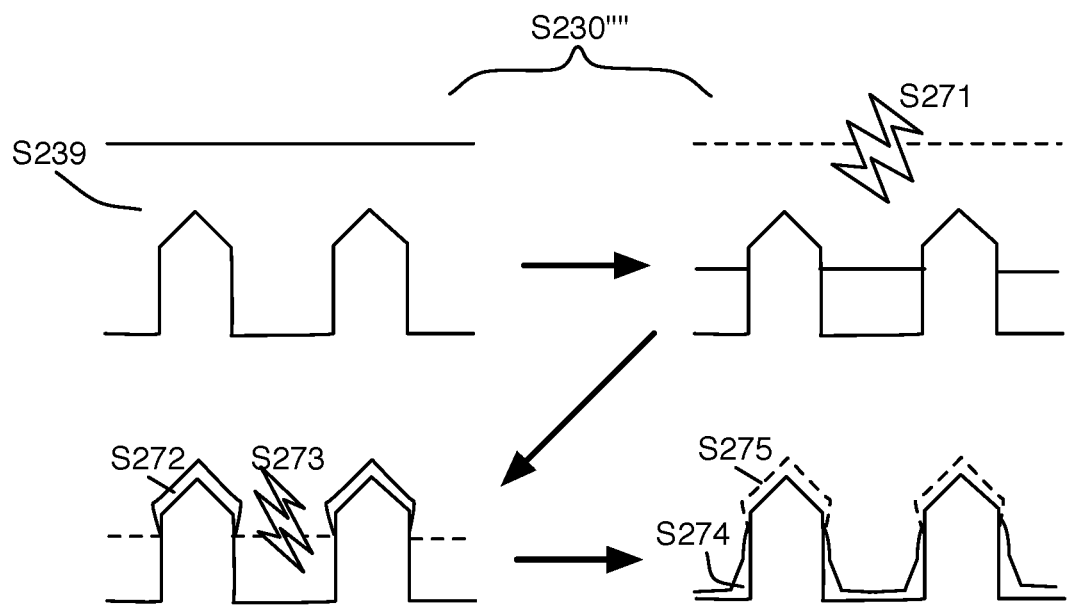

In a fifth example of Block S230'''', as shown in FIG. 7D, a photoresist can be applied to the substrate or substrate/conductive layer subassembly S239, and then etched away to expose filament tips S271. The tips may then be protected with a intermediary layer (e.g., metal or soluble insulator) S272, the photoresist can be removed by further etching S273, and then non-tip regions may then be passivated to form non-active insulating regions S274. Finally, the intermediary layer can be removed to define the active regions S275. Block S230 can alternatively comprise any other suitable method of defining an active region and a non-active region of the filament with an insulating layer.

In a sixth example of Block S230''''', the insulating material (e.g., parylene) used to define the active regions and non-active regions can also be deposited by a chemical vapor deposition (CVD) process. In this example, the tips of the filaments can be protected with a temporary protective layer (e.g., by covering each needle tip photolithographically using photoresist or applying a small droplet of photoresist or other soluble polymer to each filament tip). Then, the insulating material (e.g., parylene) can be deposited in a CVD process to conformally coat the unprotected filament areas. After deposition of the insulating material, the temporary protective layer can be removed (e.g., by using an appropriate solvent), to form the active and the non-active regions.

In variations of the method 200, Blocks S220 and S230 can be performed in any suitable order, in relation to defining an array of sharp tips in variations of Block S210, and in order to define active/non-active regions. In a first variation of the method 200, forming an array of columnar protrusions S211*b* at the substrate can be performed prior to forming an insulating layer at exposed surfaces of the substrate in Block S230. Then, the insulating layer can be selectively removed, as desired, from surfaces of the substrate (e.g., at a surface of the substrate directly opposing that of the array of columnar protrusions). After selective removal of the insulating layer, an array of sharp protrusions can be formed at distal ends of the array of columnar protrusions in variations of the method including Block S211*a*, and the conductive layer can be coupled to all regions of the substrate not covered by the insulating layer, thereby coupling the conductive layer to at least the tip regions of the array of protrusions in a variation of Block S220. As such, active region/non-active regions can be defined through bulk material removal (e.g., cutting, dicing) or any other suitable process including one or more of: selective chemical etching, plasma etching, high energy etching, and any other suitable etching method.

In a second variation, which can extend from the first variation, the method 200 can include Blocks S210, S220, and S230, and further include using a sacrificial layer to selectively isolate a region of the substrate during processing S283, in order to facilitate processing of the conductive layer and/or the insulating layer in Blocks S220 and S230, respectively. The sacrificial layer can include a nitride material (e.g., 1000-2500 Å thick nitride), an oxide material, a carbide material, a salt, a sugar, a polymer (e.g., polyethylene glycol), and/or any other suitable material that does not deteriorate during subsequent processing steps. Furthermore, the sacrificial layer can be bioabsorbable and/or porous to facilitate biocompatibility and/or processing. In one example, forming an array of sharp protrusions S211*a* can be performed prior to coupling a conductive layer to the array of sharp protrusions and any other desired surface of the substrate (e.g., a surface directly opposing that of the array of sharp protrusions), as in variations of Block S230, followed by coupling of a sacrificial layer to all surfaces of the substrate with the conductive layer. In this example, an array of columnar protrusions can be formed as in Block S211*b* by removing material between the array of sharp protrusions, after which an insulating layer can be generated at all exposed surfaces of the substrate, as in Block S230. The sacrificial layer can then be removed prior to subsequent processing steps. In another example, forming an array of sharp protrusions S211*a* can be performed prior to coupling of a sacrificial layer, as in Block S283, at all surfaces of the substrate intended to be coupled to a conductive layer. Material can then be removed between the array of sharp protrusions to form an array of columnar protrusions, as in Block S211*b*, after which an insulating layer can be formed at all exposed surfaces of the substrate, as in Block S230. Then, the sacrificial layer can be removed and the conductive layer can be coupled to all regions of the substrate formerly occupied by the sacrificial layer, as in variations of Block S220. In other examples, coupling of the sacrificial layer can be omitted or performed at any suitable stage of the method 200, specific examples of which are described in further detail below.

Figure 8A:
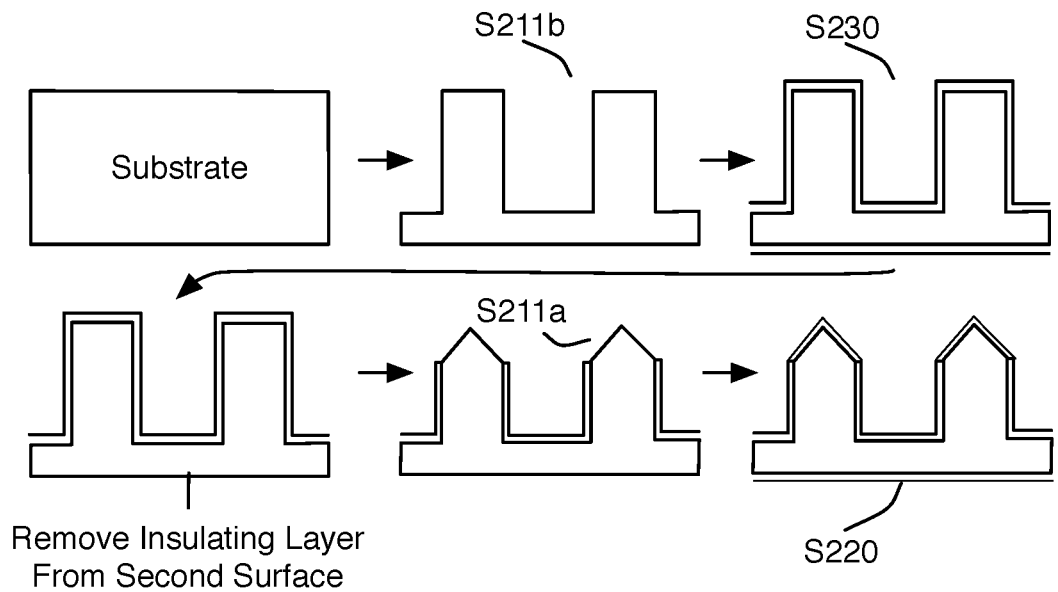
FIGS. 8A-8E depict variations of a portion of an embodiment of a method for an on-body microsensor for biomonitoring.

As shown in FIG. 8A, in a first specific example of processing the substrate, the conductive layer, and the sensing layer in Blocks S210, S220, and S230, material is removed from a first surface of the substrate, thereby forming an array of columnar protrusions as in Block S211*b*. Removing material in the first specific example is performed by way of a non-angled blade of a dicing saw in order to remove material from the first surface of the substrate to a desired depth of ~400 µm, a width of 100 µm, and a gap of 500 µm, at a cutting rate of 2-3 mm/s. In the first specific example, the dicing saw is configured to form the array of columnar protrusions through adjacent cuts in a first direction, followed by adjacent cuts in a second direction orthogonal to the first direction, thereby forming a 2-dimensional array of columnar protrusions. In the first specific example, the substrate is composed of P-type, boron-doped, <100> orientation silicon with a resistivity of 0.005-0.01 ohm-cm, a thickness from 500-1500 µm, a total thickness variation (TTV) of <10 µm, and with a first surface side polish. Subsequent to formation of the array of columnar protrusions, an insulating layer of ~1 µm oxide is formed at all exposed surfaces of the substrate, as in Block S240, by inducing thermal oxide growth at 900-1050 C for 1-2 hours. Then, the insulating layer is removed from a second surface of the substrate, directly opposing the surface of the substrate at which the columnar protrusions were formed, by way of a directed plasma etch. Subsequently, an array of sharp protrusions is formed, as in Block S211*a*, by removing material from the distal end of each columnar protrusion. Forming an array of sharp protrusions is performed by way of a 500 µm, 60-degree angled blade of a dicing saw configured to cut 2-facet tips at a rate of 4 mm/s. Similar to forming the array of columnar protrusions, the dicing saw is configured to form the array of sharp protrusions through adjacent cuts in a first direction, followed by adjacent cuts in a second direction orthogonal to the first direction, thereby forming a 2-dimensional array of sharp protrusions (i.e., sharp tips). Lastly, in the first specific example, a conductive layer is coupled to the array of sharp protrusions and the second surface of the substrate by electroplating (e.g., of nickel, of gold, and/or of platinum), as in Block S220.

Figure 8B:
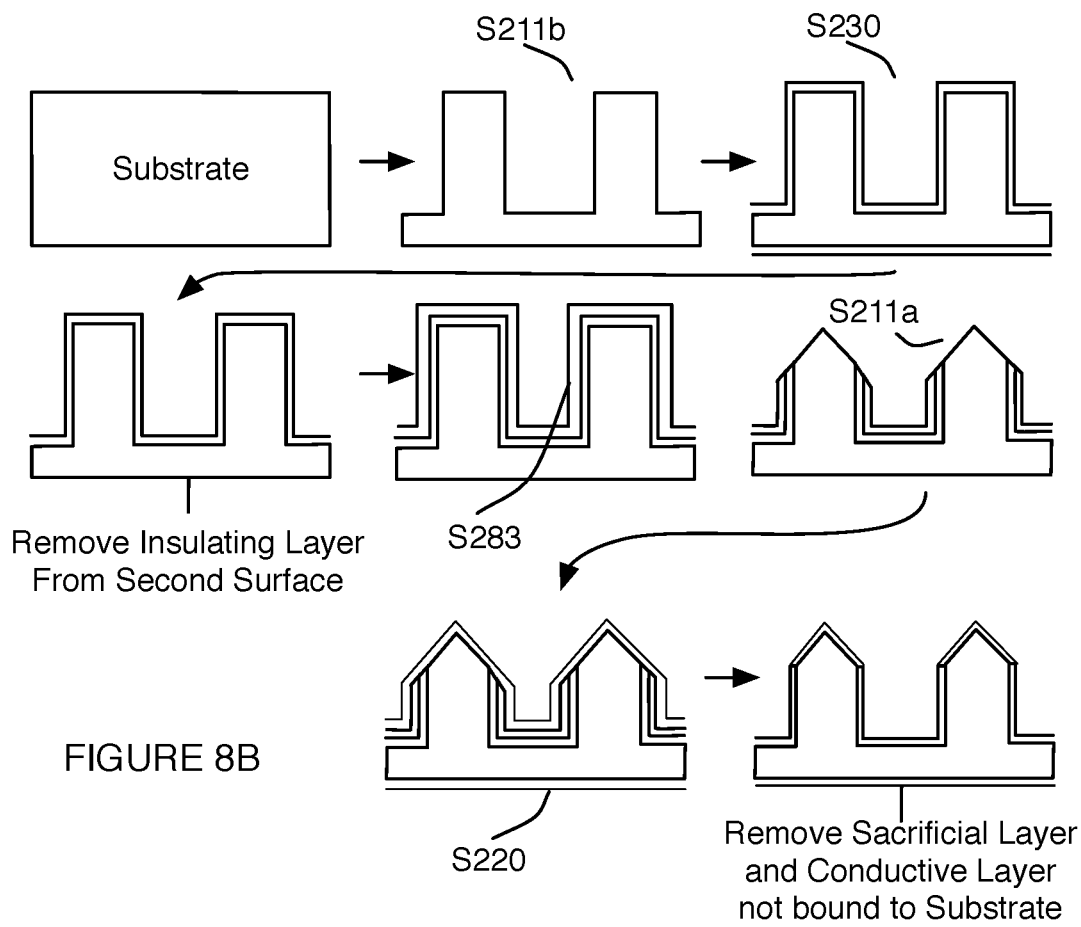

As shown in FIG. 8B, in a second specific example of processing the substrate, the conductive layer, and the sensing layer in Blocks S210, S220, and S230, material is removed from a first surface of the substrate, thereby forming an array of columnar protrusions as in Block S211*b*. Removing material in the second specific example is performed by way of a non-angled blade of a dicing saw in order to remove material from the first surface of the substrate to a desired depth of ~400 µm, a width of 100 µm, and a gap of 500 µm, at a cutting rate of 2-3 mm/s. In the second specific example, the dicing saw is configured to form the array of columnar protrusions through adjacent cuts in a first direction, followed by adjacent cuts in a second direction orthogonal to the first direction, thereby forming a 2-dimensional array of columnar protrusions. In the second specific example, the substrate is composed of P-type, boron-doped, <100> orientation silicon with a resistivity of 0.005-0.01 ohm-cm, a thickness from 500-1500 µm, a total thickness variation (TIV) of <10 µm, and with a first surface side polish. Subsequent to formation of the array of columnar protrusions, an insulating layer of ~1 µm oxide is formed at all exposed surfaces of the substrate, as in Block S230, by inducing thermal oxide growth at 900-1050 C for 1-2 hours. Then, the insulating layer is removed from a second surface of the substrate, directly opposing the surface of the substrate at which the columnar protrusions were formed, by way of a directed plasma etch. Following removal of the insulating layer from the second surface, a sacrificial layer is coupled to all surfaces of the substrate still coupled to the insulating layer. Subsequently, an array of sharp protrusions is formed, as in Block S211*a*, by removing material from the distal end of each columnar protrusion. Forming an array of sharp protrusions is performed by way of a 500 µm, 60-degree angled blade of a dicing saw configured to cut 2-facet tips at a rate of 4 mm/s. Similar to forming the array of columnar protrusions, the dicing saw is configured to form the array of sharp protrusions through adjacent cuts in a first direction, followed by adjacent cuts in a second direction orthogonal to the first direction, thereby forming a 2-dimensional array of sharp protrusions (i.e., sharp tips). Lastly, in the second specific example, a conductive layer is coupled to the array of sharp protrusions and the second surface of the substrate by electroplating (e.g., of nickel, of gold, and/or of platinum) as in Block S220, followed by removal of the sacrificial layer from the insulating layer. The sacrificial layer, in the second specific example, thus functions to facilitate isolation of the conductive layer to desired surfaces, such that the conductive layer does not substantially overlap with the insulating layer in an undesired manner.

Figure 8C:
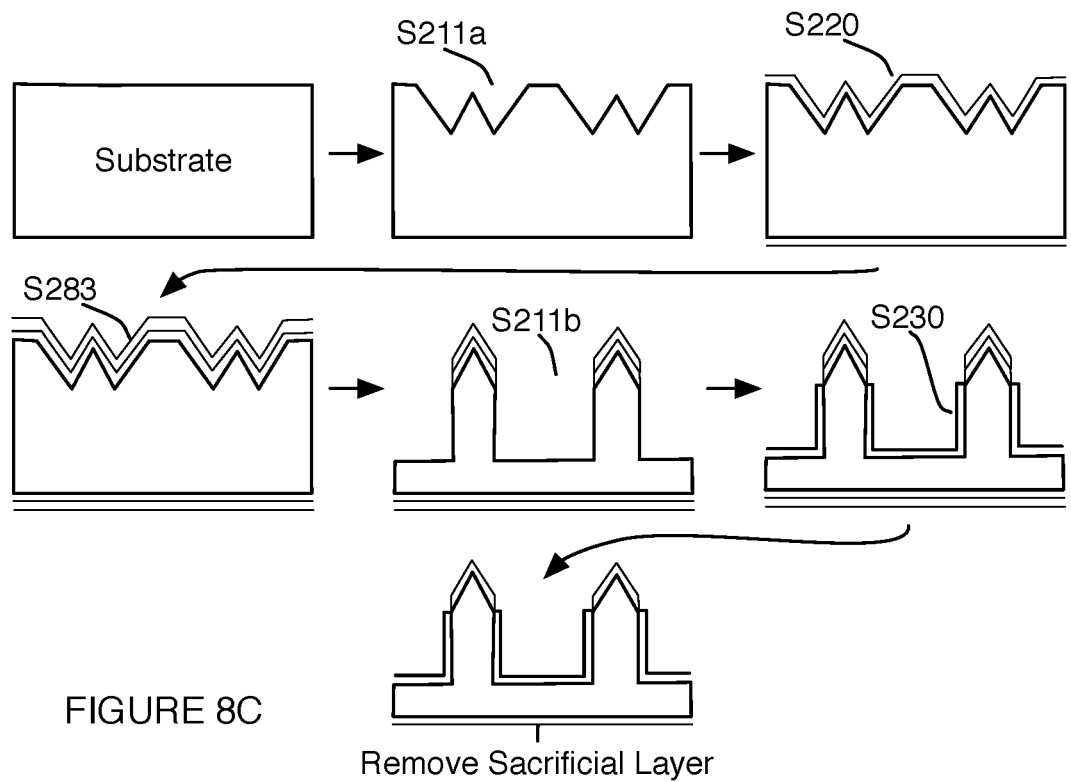

As shown in FIG. 8C, in a third specific example of processing the substrate, the conductive layer, and the sensing layer in Blocks S210, S220, and S230, material is removed from a first surface of the substrate to form an array of sharp protrusions (e.g., sharp tips), as in Block S211a. Forming an array of sharp protrusions is performed by way of a 500 µm, 60-degree angled blade of a dicing saw configured to cut 2-facet tips at a rate of 4 mm/s. In the third specific example, the dicing saw is configured to form the array of sharp protrusions through adjacent cuts in a first direction, followed by adjacent cuts in a second direction orthogonal to the first direction, thereby forming a 2-dimensional array of sharp protrusions. In the third specific example, the substrate is composed of P-type, boron-doped, <100> orientation silicon with a resistivity of 0.005-0.01 ohm-cm, a thickness from 500-1500 µm, a total thickness variation (TIV) of <10 µm, and with a first surface side polish. Subsequent to forming the array of sharp protrusions, a conductive layer is coupled to the array of sharp protrusions and a second surface of the substrate, directly opposed to the array of sharp protrusions, as in Block S220, by depositing 1000 Å of platinum, 1000 Å of iridium, 1000 Å of tungsten, and 100Å of titanium nitride at the desired surfaces. In variations of the third specific example, the conductive layer can include: a 10000 Å thick platinum layer and a 100 Å thick titanium layer, a 10000 Å thick platinum layer and a 100 Å thick titanium nitride layer, a 10000 Å thick iridium layer and a 100 Å thick titanium nitride layer, or a 10000 Å thick tungsten layer. A sacrificial layer comprising a 1000-2500 Å thick layer of nitride is then coupled to the conductive layer, as in Block S283, and material is removed from the substrate between each sharp protrusion in the array of sharp protrusions, thereby forming an array of columnar protrusions coupled to the array of sharp protrusions, as in Block S211b. Forming the array of columnar protrusions is performed by way of a non-angled blade of a dicing saw in order to remove material from the first surface of the substrate to a desired depth of ~400 µm, a width of 100 µm, and a gap of 500 µm, at a cutting rate of 2-3 mm/s. In the third specific example, the dicing saw is configured to form the array of columnar protrusions through adjacent cuts in a first direction, followed by adjacent cuts in a second direction orthogonal to the first direction, thereby forming a 2-dimensional array of columnar protrusions. An insulating layer is formed at all exposed surfaces (e.g., cut surfaces without conductive layer or sacrificial layer) of the substrate, as in Block S230, by inducing thermal oxide growth to a thickness of 1 µm at 900-1050 C for 1-2 hours. Then, the sacrificial layer is removed by a directed plasma etch.

Figure 8D:
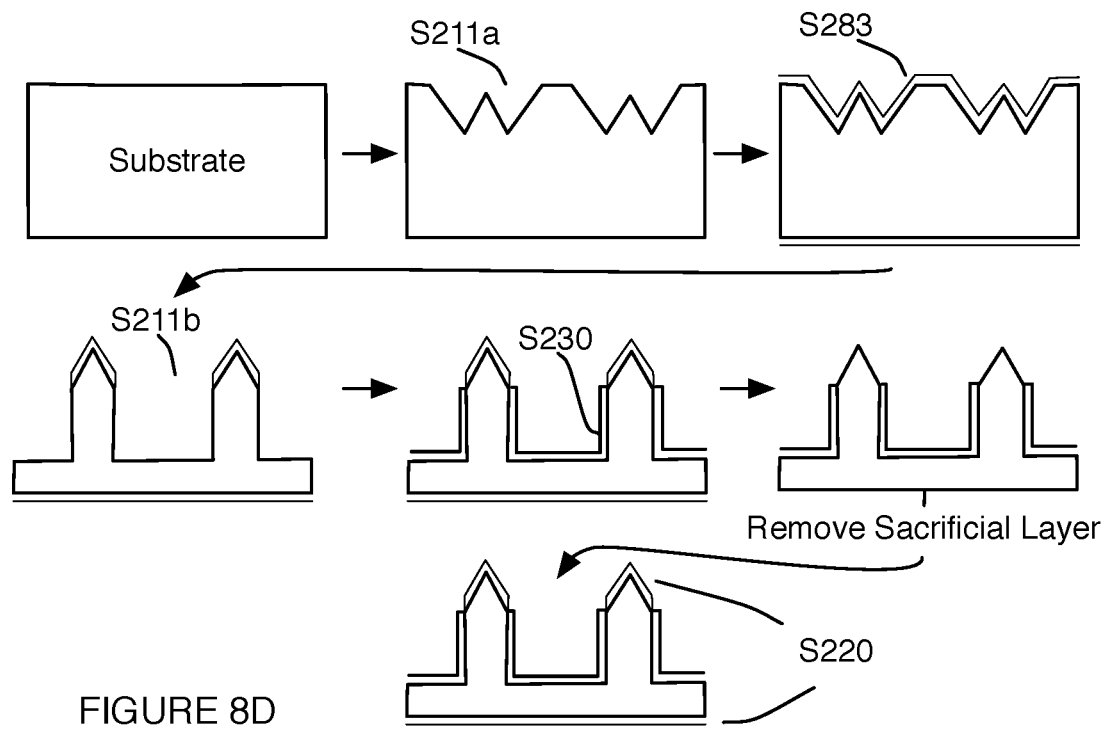

As shown in FIG. 8D, in a fourth specific example of processing the substrate, the conductive layer, and the sensing layer in Blocks S210, S220, and S230, material is removed from a first surface of the substrate to form an array of sharp protrusions (e.g., sharp tips), as in Block S211a. Forming an array of sharp protrusions is performed by way of a 500 µm, 60-degree angled blade of a dicing saw configured to cut 2-facet tips at a rate of 4 mm/s. In the fourth specific example, the dicing saw is configured to form the array of sharp protrusions through adjacent cuts in a first direction, followed by adjacent cuts in a second direction orthogonal to the first direction, thereby forming a 2-dimensional array of sharp protrusions. In the fourth specific example, the substrate is composed of P-type, boron-doped, <100> orientation silicon with a resistivity of 0.005-0.01 ohm-cm, a thickness from 500-1500 µm, a total thickness variation (TIV) of <10 µm, and with a first surface side polish. A sacrificial layer comprising a 1000-2500 Å thick layer of nitride is then coupled to the array of sharp protrusions and to a second surface of the substrate directly opposing the array of sharp protrusions, as in Block S283, and material is removed from the substrate between each sharp protrusion in the array of sharp protrusions, thereby forming an array of columnar protrusions coupled to the array of sharp protrusions, as in Block S211b. Forming the array of columnar protrusions is performed by way of a non-angled blade of a dicing saw in order to remove material from the first surface of the substrate to a desired depth of ~400 µm, a width of 100 µm, and a gap of 500 µm, at a cutting rate of 2-3 mm/s. In the fourth specific example, the dicing saw is configured to form the array of columnar protrusions through adjacent cuts in a first direction, followed by adjacent cuts in a second direction orthogonal to the first direction, thereby forming a 2-dimensional array of columnar protrusions. An insulating layer is formed at all exposed surfaces (e.g., cut surfaces without sacrificial layer) of the substrate, as in Block S230, by inducing thermal oxide growth to a thickness of 1 µm at 900-1050 C for 1-2 hours. Then, the sacrificial layer is removed by a directed plasma etch. Subsequent to removal of the sacrificial layer, a conductive layer is coupled to the array of sharp protrusions and a second surface of the substrate, directly opposed to the array of sharp protrusions, as in Block S220, by depositing 1000 Å of platinum, 1000 Å of iridium, 1000 Å of tungsten, and 100 Å of titanium nitride at the desired surfaces. In variations of the fourth specific example, the conductive layer can include: a 10000 Å thick platinum layer and a 100 Å thick titanium layer, a 10000 Å thick platinum layer and a 100 Å thick titanium nitride layer, a 10000 Å thick iridium layer and a 100 Å thick titanium nitride layer, or a 1000 Å thick tungsten layer. Other variations of the fourth specific example can include electroplating of any suitable metal (e.g., nickel, gold, platinum).

Figure 8E:
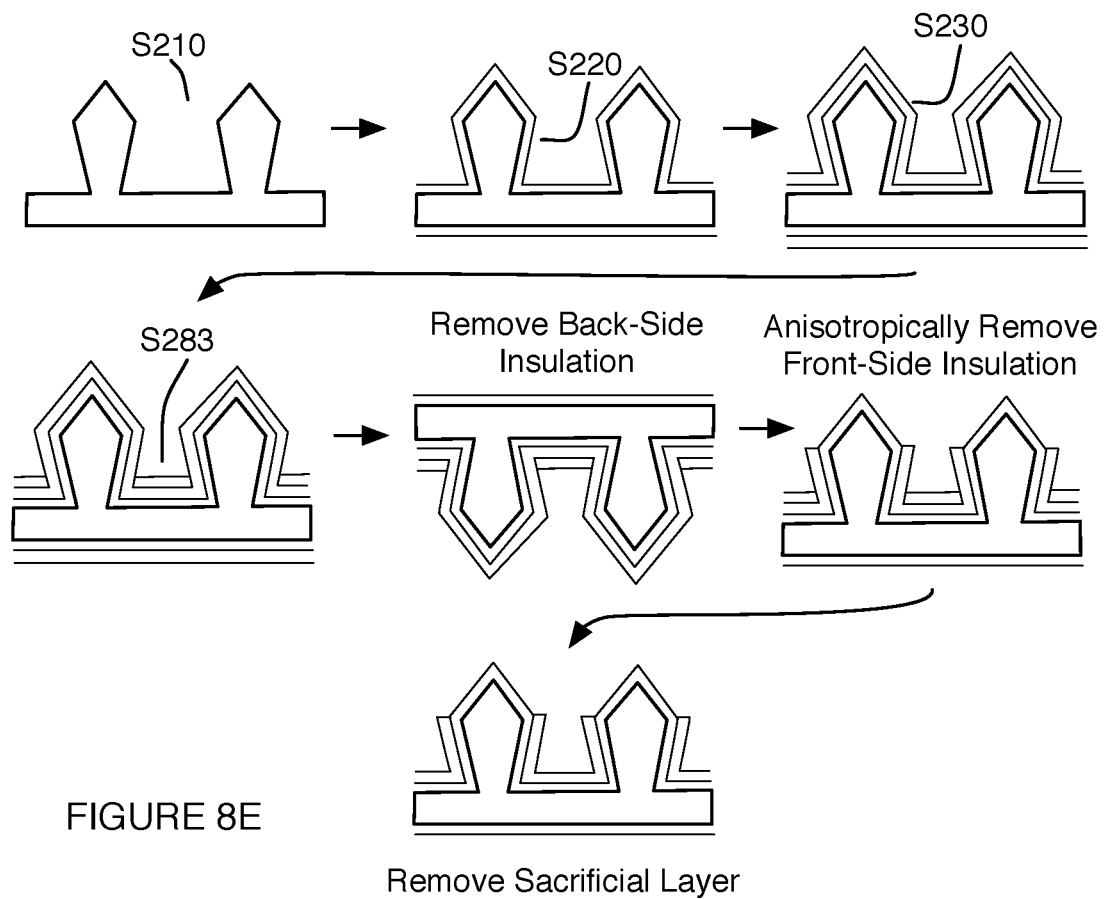

As shown in FIG. 8E, in a fifth specific example of processing the substrate, the conductive layer, and the sensing layer in Blocks S210, S220, and S230, an array of sharp protrusions, with a tapered profile (i.e., tapering from a tip end toward a base end coupled to the substrate), is formed at a first surface of a substrate by a DRIE process, as in Block S210. A conductive layer is then coupled to all exposed surfaces of the substrate, as in Block S220 by depositing 1000 Å of platinum, 1000 Å of iridium, 1000 Å of tungsten, and 100 Å of titanium nitride at the exposed surfaces. In variations of the fifth specific example, the conductive layer can include: a 10000 Å thick platinum layer and a 100 Å thick titanium layer, a 10000 Å thick platinum layer and a 100 Å thick titanium nitride layer, a 10000 Å thick iridium layer and a 100 Å thick titanium nitride layer, or a 10000 Å thick tungsten layer. Other variations of the fifth specific example can include electroplating of any suitable metal (e.g., nickel, gold, platinum) to form the conductive layer. Subsequent to formation of the conductive layer, an insulating layer comprising a nitride material is then coupled to the conductive layer, as in Block S230, and a sacrificial layer is then coupled to the insulating layer, as in Block S283, at regions of the substrate between the base ends of the array of sharp protrusions. In the fifth specific example, the sacrificial layer is applied by way of a spin photoresist. Subsequently, the insulating layer is removed from the tip regions of the array of sharp protrusions and from a second surface of the substrate, directly opposed to the array of sharp protrusions, by way of an anisotropically directed plasma field. Lastly, the sacrificial layer is removed (e.g., by etching).

In other examples of the method 200, processing the substrate, the conductive layer, and the sensing layer in Blocks S210, S220, and S230 can be performed according to any other suitable process and in any other suitable order. Furthermore, in variations of the described processes, any suitable number of blades, cutting surfaces, other tool for removal of material can be used to increase processing speed/efficiency.

2.2 Manufacturing Method—Sensing Layer and Selective Layer Processing

Block S240 recites applying a sensing layer to at least the conductive layer, and functions to form a filament coating that enables transduction of an ionic concentration to an electronic voltage. Preferably, the sensing layer is applied selectively to the filament substrate/conductive layer/insulating layer assembly at regions where the conductive layer is exposed (e.g., only at active regions); however, the sensing layer can alternatively be applied to the entire filament substrate/conductive layer/insulating layer assembly. In variations wherein the sensing layer is applied selectively to the filament substrate/conductive layer/insulating layer assembly, Block S240 can comprise electrodeposition, lithography, inkjet printing, screen printing, or any other appropriate method for applying the sensing layer selectively. In variations wherein the sensing layer is applied to the entire filament substrate/conductive layer/insulating layer assembly, Block S240 can comprise glazing, spin coating, spray coating, or any method of applying a polymer coating in a non-selective manner. Preferably, the sensing layer is composed of a material with reversible redox reaction behavior, as previously described. In one example, the sensing layer can comprise a nitrogen-containing polymer, such as polypyrrole or polyaniline. The sensing layer can additionally or alternatively be composed of any appropriate conductive material. In another example, the sensing layer can additionally or alternatively comprise a protein or peptide serving as a complementary molecule to an analyte, such as glucose oxidase for glucose sensing or valinomycin for potassium sensing. In variations of this example, the sensing layer can comprise amino acids (e.g., lysine) and/or polymer chains of subsequently associated amino acids (e.g., poly-lysine). In providing a protein distribution, an amino acid distribution, a polymer chain distribution, and/or any other particle distribution at the sensing layer in Block S240, the distribution can be uniform or non-uniform (e.g., concentrated in desired regions, concentrated at a surface, etc.), homogenous or heterogeneous, and generated in any suitable manner.

Figure 9:
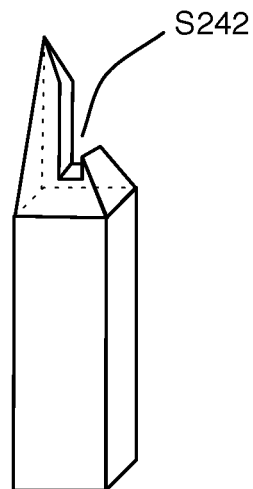
FIG. 9 depicts a portion of an embodiment of a method for an on-body microsensor for biomonitoring.

In some variations, Block S240 can include forming a notch at least at one sharp protrusion (i.e., sharp tip) of the array of sharp protrusions S242 formed, as in Block S211a. The notch, as shown in FIG. 9, can be used as a pocket to isolate the sensing layer, and can additionally or alternatively be filled with any other suitable functional material. In one such variation, the notch can be filled with a protective material that functions to protect the sensing layer during insertion or during a period of contact with the user's body fluid. In another variation, the notch can be filled with a "calibration material" configured to provide or release an analyte according to a known profile (e.g., release profile, concentration, degradation profile, etc.). In another variation, the notch can be filled with a therapeutic substance to facilitate delivery of the therapeutic substance to a user in a drug delivery application. The notch can be formed in alignment with a sharp tip of a filament, or can alternatively be form in misalignment with a warp tip of a filament. Variations of Block S240 can entirely omit forming the notch, or can including providing a notch for any other suitable purpose.

Some variations of the method can further include Block S245, which recites: coupling an intermediate selective layer to the conductive layer defined in Block S220. In a variation wherein another layer (e.g., an intermediate active layer that facilitates transduction, as described in Section 1 above) is coupled superficial to the conductive layer defined in Block S220, the method can include a variation of Block S245 as Block S246, which recites: providing an intermediate selective layer able to transmit a signal to the conductive layer, and coupling the sensing layer defined in Block S240 to the intermediate selective layer. Blocks S245 and S246 function to provide an additional selective layer to facilitate detection of an analyte (e.g., glucose) in a selective manner. In some variations, Blocks S245 and S246 can include applying a polymer superficial to the conductive layer, and polymerizing the polymer to set the intermediate selective layer. In specific examples of Blocks S245 and S246, the intermediate selective layer can include phenylenediamine for glucose sensing, which is electropolymerized to set the intermediate selective layer. Other variations of these specific examples can include polymerization of any other suitable material in any other suitable manner (e.g., chemical polymerization, heat polymerization, photopolymerization, etc.). Other variations of Blocks S245 and S246 can alternatively include providing a non-polymeric material as the intermediate sensing layer, which can be processed in any other suitable manner.

Block S250 recites forming a selective layer, and functions to form a layer configured to facilitate sensing of specific target analytes. Preferably, Block S250 comprises forming a selective layer comprising a polymer matrix with a distribution of complementary molecules S252 to at least one target analyte characterizing a user's body chemistry. Block S252 preferably comprises forming a homogenous mixture of the polymer matrix material (e.g., in either a solution or gel phase) with the distribution of complementary molecules, but can alternatively comprise forming a heterogeneous mixture of the polymer matrix material with the distribution of complementary molecules. Alternatively, Block S252 can be replaced by Block S254, which comprises depositing a layer of a polymer matrix and depositing the distribution of complementary molecules, onto the assembly produced after Block S240, in any order. In still another alternative, Block S250, S252 and/or Block S254 can be performed prior to one or more of Blocks S220, S230, and S240, such that a selective layer is deposited at different times and/or different locations during processing of the microsensor. In one such example, in a sensor for glucose detection applications, Block S250 is performed subsequent to Block S220 (e.g., immediately over the conductive layer).

In another example, with a conductive substrate, Block S250 can be performed subsequent to Block S210 (e.g., a selective layer can be deposited onto a tip region of the conductive substrate). Forming a selective layer comprising a polymer matrix can further comprise forming a selective layer with a polymer matrix and a plasticizer, in embodiments wherein a flexible polymer matrix is desired for Block S250. In one specific example, the polymer matrix comprises polyvinyl chloride (PVC) with a plasticizer to increase flexibility; however, in other variations, the polymer matrix can be composed of any appropriate polymer (e.g., polyethylene, polytetrafluoroethylene, urethane, polyurethane, phenylenediamine, ortho-phenylenediamine, protein matrices, amino acid matrices, etc.), with or without a plasticizer, and configured to contain a distribution of complementary molecules. Again, in one example, the distribution of complementary molecules comprises glucose oxidase molecules for glucose sensing, and in another example, the distribution of complementary molecules comprises valinomycin molecules for potassium sensing. Block S250 can be performed by spin coating a polymer matrix-complementary molecule mixture with or without a plasticizer, by drop casting a polymer matrix-complementary molecule mixture with or without a plasticizer, or by any appropriate method. Additionally, spin coating, drop casting, electrodeposition, electroplating, or any other suitable method of application can be performed in stages, such that the selective layer is characterized by a tunable thickness. The tunable thickness preferably governs a rate at which complementary molecules bind to target analytes (e.g., diffusion rate), and governs the amount (e.g., concentration or total amount) of complementary molecules within the selective layer and/or defines a molecular size cut-off.

In some variations, in particular, variations of manufacturing a microsensor for glucose sensing, the method 200 can additionally or alternatively include Block S256, which recites: providing a stabilizing layer configured to stabilize the sensing layer. Block S256 preferably functions to stabilize a glucose oxidase sensing layer, in manufacturing a microsensor for glucose sensing; however, Block S256 can additionally or alternatively function to stabilize the sensing layer for any other suitable application. In some variations, Block S256 can include providing a polymer superficial to the sensing layer, and polymerizing the polymer to set the intermediate selective layer. In specific examples of Block S256, the stabilizing layer can include phenylenediamine for glucose sensing, which is electropolymerized to set the stabilizing layer. Other variations of this specific example can include polymerization of any other suitable material in any other suitable manner (e.g., chemical polymerization, heat polymerization, photopolymerization, etc.). Other variations of Block S256 can alternatively include providing a non-polymeric material as the intermediate sensing layer, which can be processed in any other suitable manner.

In some variations, in particular, variations of manufacturing a microsensor for glucose sensing, the method 200 can additionally or alternatively include Block S258, which recites: providing an intermediate protective layer superficial to the sensing layer. Block S258 preferably functions to form a layer that provides intermediate protection and/or block transport of undesired species. In some variations, Block S258 can include providing a polymer superficial to the sensing layer, including at least one functional compound configured to provide a protective barrier. In examples, the polymer of the intermediate protective layer can include any one or more of: teflon, chlorinated polymer, nafion, polyethylene glycol, and any other suitable polymer, and can include functional compounds including one or more of: lipids, charged chemical species that block transport of charged species, surfactants, and any other suitable compound. Other variations of Block S258 can alternatively include providing a non-polymeric material as the intermediate protective layer, which can be processed in any other suitable manner.

The method 200 can additionally or alternatively include any other suitable Blocks or Steps configured to generate an array of filaments for analyte sensing during contact with a body fluid of the user. As such, the method 200 can include any one or more of: coupling an adhesion layer to any suitable layer used during the method, wherein the adhesion layer functions to facilitate maintenance of coupling of the layer(s) for robustness; coupling a temporary functional layer to the selective layer, which facilitates penetration into the body of the user and/or calibration of the microsensor; providing a functional external layer configured to suppress or prevent an inflammatory response (e.g., by comprising a surface treatment or an anti-inflammatory agent), prevent bio-rejection, prevent encapsulation (e.g., by comprising a bio-inert substance, such as pyrolytic carbon), enhance target analyte/ion detection, and/or provide any other suitable anti-failure mechanism; and processing the substrate according to any other suitable process.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The present application is related to U.S. patent application Ser. No. 16/722,977 filed Dec. 20, 2019, which is a continuation of U.S. patent application Ser. No. 14/876,692 filed 6 Oct. 2015, which is a continuation of U.S. patent application Ser. No. 14/211,404, filed 14 Mar. 2014, which claims the benefit of U.S. Provisional Application Ser. No. 61/905,583, filed on 18 Nov. 2013 and U.S. Provisional Application Ser. No. 61/781,754, filed on 14 Mar. 2013, which are all incorporated herein in their entirety by reference.

As a person skilled in the art will recognize from the previous detailed description and from the figures and claims, modifications and changes can be made to the preferred embodiments of the invention without departing from the scope of this invention defined in the following claims.

What is claimed is:

1. A method for manufacturing an analyte sensor, the method comprising:
    removing material from a substrate to form needle bodies of an array of microneedles;

removing material from each of the needle bodies using at least one saw to form sharp tips of the microneedles;

removing material from the needle bodies to expose conductive layers of the needle bodies, wherein the needle bodies are columnar protrusions; and forming at least one layer along at least one of the sharp tips, wherein the at least one layer is configured to detect at least one analyte in interstitial fluid when the analyte sensor is located along a user's skin.

2. The method of claim 1, further comprising applying one or more layers to the needle bodies prior to removing the material from each of the needle bodies.

3. The method of claim 2, wherein the one or more layers include an insulating layer and a conductive layer.

4. The method of claim 1, further comprising removing the material from the substrate via an etching process.

5. The method of claim 1, wherein the at least one layer extends along a length of at least one of the needle bodies.

6. The method of claim 1, further comprising removing the material from the substrate using laser etching.

7. The method of claim 1, further comprising punching, die-cutting, and/or water cutting the substrate to form at least a portion of the microneedles.

8. The method of claim 1, further comprising electrically coupling the substrate to an electrical component.

9. The method of claim 1, further comprising forming a plurality of layers on at least a portion of the microneedles.

10. The method of claim 1, further comprising electrically coupling the array of microneedles to an electronics circuit.

11. The method of claim 1, wherein the microneedles have a height within a range from 150 microns to 500 microns.

12. The method of claim 1, wherein the substrate includes at least one of a semiconducting material, a conducting material, or an insulating material.

13. The method of claim 1, wherein the analyte sensor is a single analyte sensor.

14. The method of claim 1, wherein the analyte sensor is a multiple analyte sensor.

15. The method of claim 1, further comprising setting a cutting angle of the at least one saw to form the sharp tips after removing the material from the substrate to form the needle bodies.

16. A method for manufacturing a microneedle sensor, the method comprising:

removing material from a substrate to form needle bodies;

removing material from the needle bodies to form sharp ends and to expose conductive layers; and after forming the sharp ends, forming at least one catalyst layer along each of the sharp ends of the needle bodies, wherein the at least one catalyst layer is configured to facilitate detection of at least one analyte in interstitial fluid.

17. The method of claim 16, further comprising forming an insulating layer along at least one of the needle bodies.

18. The method of claim 16, further comprising removing the material from the substrate using an etching process.

19. The method of claim 16, further removing the material from the substrate using a laser etching process.

20. The method of claim 16, further comprising punching, die-cutting, laser cutting, molding, and/or water cutting the substrate to form at least a portion of the microneedles.

21. A method for manufacturing an analyte sensor with microneedles, the method comprising:

using at least one saw to cut material from a substrate to form an array of needle bodies and to cut the material from needle bodies;

forming sharp tips of the needle bodies; and forming at least one catalyst layer at each of the sharp ends, wherein the at least one catalyst layer is configured to react with at least one analyte in interstitial fluid.

22. The method of claim 21, further comprising forming an insulating layer and a conductive layer along each of the microneedles.

23. The method of claim 21, wherein a plurality of layers are located on a sidewall of the needle bodies, and the plurality of layers include a conductive layer and an insulating layer.

24. The method of claim 21, further comprising cutting material from the needle bodies to form the sharp tips.

25. The method of claim 21, wherein the microneedles include one or more layers extending along lengths of the needle bodies.

26. The method of claim 21, wherein the analyte sensor is configured to detect different analytes.

27. A method for manufacturing an analyte sensor with microneedles, the method comprising:

removing material from a substrate to form an array of needle bodies;

forming sharp tips of the needle bodies;

forming at least one catalyst layer at each of the sharp ends, wherein the at least one catalyst layer is configured to react with at least one analyte in interstitial fluid; and wherein the material is removed from the needle bodies so as to expose at least one conductive layer of the microneedles.

28. The method of claim 27, wherein the removed material is etched from the substrate.

29. The method of claim 27, wherein one or more of the microneedles has a height within a range from 150 microns to 500 microns.

30. The method of claim 27, wherein one or more of the microneedles has a height within a range from 250 microns to 350 microns.

\* \* \* \* \*

UNITED STATES PATENT AND TRADEMARK OFFICE
CERTIFICATE OF CORRECTION

PATENT NO. : 11,197,985 B2
APPLICATION NO. : 17/125999
DATED : December 14, 2021
INVENTOR(S) : Ashwin Pushpala et al.

It is certified that error appears in the above-identified patent and that said Letters Patent is hereby corrected as shown below:

In the Specification

In Column 4, Line 12, delete "no" and insert -- 110 --.

In Column 4, Line 15, delete "no" and insert -- 110 --.

In Column 4, Line 20, delete "no" and insert -- 110 --.

In Column 4, Line 21, delete "no" and insert -- 110 --.

In Column 4, Line 23, delete "no" and insert -- 110 --.

In Column 4, Line 24, delete "no" and insert -- 110 --.

In Column 4, Line 39, delete "no" and insert -- 110 --.

In Column 6, Line 15, delete "(TIV)" and insert -- (TTV) --.

In Column 7, Line 14, delete "m)," and insert -- µm), --.

In Column 8, Line 1, delete "gluteraldehyde," and insert -- glutaraldehyde, --.

In Column 8, Lines 3-4, delete "phenylenediamene," and insert -- phenylenediamine, --.

In Column 8, Line 13, after "alternatively" delete "be".

In Column 9, Line 10, delete "mediatior" and insert -- mediator --.

In Column 9, Line 52, delete "paralyene," and insert -- parylene, --.

Signed and Sealed this
Thirty-first Day of January, 2023

Katherine Kelly Vidal
*Director of the United States Patent and Trademark Office*

CERTIFICATE OF CORRECTION (continued)
U.S. Pat. No. 11,197,985 B2

In Column 11, Line 25, delete "can isolated" and insert -- can be isolated --.

In Column 12, Line 40, delete "TIV" and insert -- TTV --.

In Column 12, Line 64, after "120" delete "is".

In Column 13, Line 10, delete "TIN" and insert -- TTV --.

In Column 13, Line 27, delete "phenylenediamene," and insert -- phenylenediamine, --.

In Column 15, Line 42, delete "TIN" and insert -- TTV --.

In Column 15, Line 46, delete "TIV," and insert -- TTV, --.

In Column 18, Line 7, delete "the a" and insert -- the --.

In Column 18, Line 29, delete "S230"," and insert -- S230'", --.

In Column 20, Line 52, delete "(TIV)" and insert -- (TTV) --.

In Column 21, Line 32, delete "(TIV)" and insert -- (TTV) --.

In Column 21, Line 38, delete "100∧" and insert -- 100Å --.

In Column 22, Line 15, delete "(TIV)" and insert -- (TTV) --.